United States Patent [19]
Ericksen et al.

[11] Patent Number: 6,128,528
[45] Date of Patent: Oct. 3, 2000

[54] ERROR CODE CALCULATIONS FOR DATA STORED IN AN IMPLANTABLE MEDICAL DEVICE

[75] Inventors: James H. Ericksen, Roseville; Carl A. Schu, Plymouth; Vincent E. Splett, Apple Valley; Paul J. Huelskamp, St. Paul, all of Minn.

[73] Assignee: Medtronics, Inc., Minneapolis, Minn.

[21] Appl. No.: 09/271,123

[22] Filed: Mar. 18, 1999

[51] Int. Cl.[7] ........................................... A61N 1/36
[52] U.S. Cl. ..................................................... 607/2
[58] Field of Search .................... 607/2, 31, 32, 607/59; 600/300

[56] References Cited

U.S. PATENT DOCUMENTS

| | | |
|---|---|---|
| 4,156,796 | 5/1979 | O'Neal et al. . |
| 4,188,665 | 2/1980 | Nagel et al. . |
| 4,484,303 | 11/1984 | Provanzano et al. . |
| 4,550,370 | 10/1985 | Baker . |
| 4,556,063 | 12/1985 | Thompson et al. . |
| 4,562,841 | 1/1986 | Brockway et al. . |
| 4,571,589 | 2/1986 | Slocum et al. . |
| 4,654,480 | 3/1987 | Weiss . |
| 4,693,253 | 9/1987 | Adams . |
| 4,754,482 | 6/1988 | Weiss . |
| 4,830,006 | 5/1989 | Haluska et al. . |
| 4,890,281 | 12/1989 | Balboni et al. . |
| 4,971,058 | 11/1990 | Pless et al. . |
| 4,991,133 | 2/1991 | Davis et al. . |
| 5,127,404 | 7/1992 | Wyborney et al. . |
| 5,132,975 | 7/1992 | Avaneas . |
| 5,167,034 | 11/1992 | MacLean, Jr. et al. . |
| 5,170,401 | 12/1992 | Mohr . |
| 5,226,137 | 7/1993 | Bolan et al. . |
| 5,307,817 | 5/1994 | Gugenbuhl et al. . |
| 5,312,441 | 5/1994 | Mader et al. . |
| 5,321,704 | 6/1994 | Erickson et al. . |
| 5,323,403 | 6/1994 | Elliott . |
| 5,331,318 | 7/1994 | Montgomery . |
| 5,342,408 | 8/1994 | deCoriolis et al. . |
| 5,363,448 | 11/1994 | Koopman, Jr. et al. . |
| 5,377,270 | 12/1994 | Koopman, Jr. et al. . |
| 5,456,692 | 10/1995 | Smith, Jr. et al. . |
| 5,459,459 | 10/1995 | Lee, Jr. . |
| 5,480,415 | 1/1996 | Cox et al. . |
| 5,508,909 | 4/1996 | Maxwell et al. . |
| 5,521,915 | 5/1996 | Dieudonne et al. . |
| 5,558,638 | 9/1996 | Evers et al. . |
| 5,598,424 | 1/1997 | Erickson et al. . |
| 5,607,458 | 3/1997 | Causey, III et al. . |
| 5,735,882 | 4/1998 | Rottenberg et al. . |
| 5,748,103 | 5/1998 | Flach et al. . |
| 5,748,649 | 5/1998 | Michel et al. . |
| 5,755,742 | 5/1998 | Schuelke et al. . |
| 5,767,791 | 6/1998 | Stoop et al. . |
| 5,787,498 | 7/1998 | Lee et al. . |
| 5,800,460 | 9/1998 | Powers et al. . |
| 5,818,822 | 10/1998 | Thomas et al. . |
| 5,827,326 | 10/1998 | Kroll et al. . |
| B1 4,830,006 | 10/1997 | Haluska et al. . |

FOREIGN PATENT DOCUMENTS 9802209   1/1998   WIPO .

Primary Examiner—William E. Kamm
Attorney, Agent, or Firm—Reed A. Duthler; Harold R. Patton

[57] ABSTRACT

A cyclic redundancy code (CRC) and optionally a syndrome value calculation of one or more implantable medical device (IMD) data block is conducted by block mover/reader hardware of the IMD when the data block(s) are moved and/or read. In the block read operation, each data byte or word in the block mover data register is read in a first clock cycle. In the block move operation, each data byte is read in the first clock cycle in this way and then moved to a destination register in a second clock cycle. The data CRC and optionally the syndrome value accumulate in the CRC and syndrome registers as all data bytes of the data block(s) are read in the first clock cycle. When the last data byte or word of the data block(s) is sequentially read (and moved in the block move operation), the accumulated data CRC and syndrome value are either stored as the associated data CRC and optional syndrome value or are used for comparison with a previously stored data CRC and optional syndrome value associated with the data block(s) in the comparison operation to determine if the data block(s) is corrupted.

33 Claims, 9 Drawing Sheets

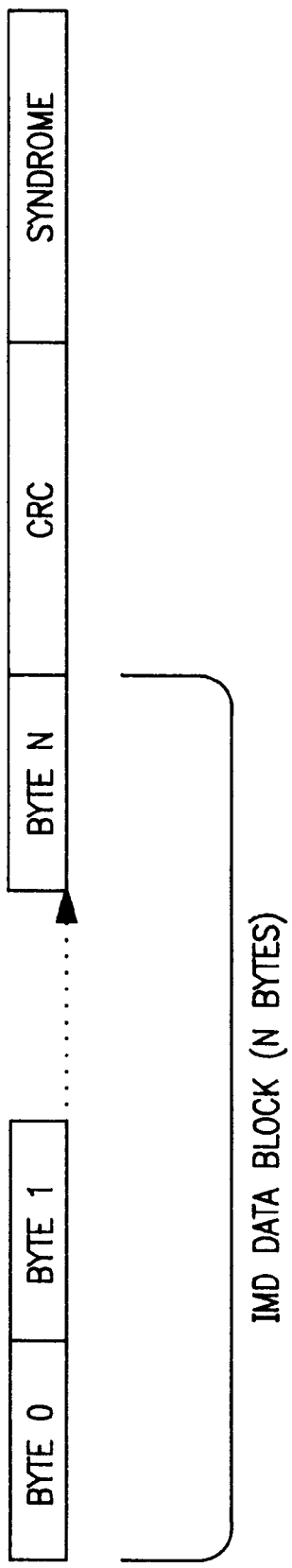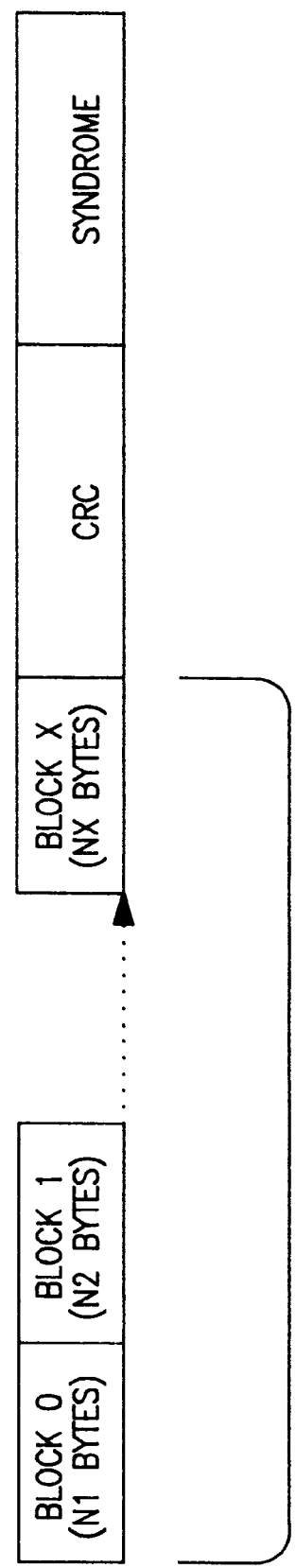

ERROR CODE CALCULATIONS FOR DATA STORED IN AN IMPLANTABLE MEDICAL DEVICE

FIELD OF THE INVENTION

This invention relates generally to implantable medical devices for providing therapies and/or monitoring physiologic conditions of a patient, and more particularly to cyclic redundancy code (CRC) and optionally syndrome value calculation of internally stored data blocks when they are stored in memory or moved from one memory location to another or are periodically read in a self check routine.

BACKGROUND OF THE INVENTION

A wide variety of implantable medical devices (IMDs) that employ electronic circuitry for providing electrical stimulation of body tissue and/or monitoring a physiologic condition are known in the art. A number of IMDs of various types are known in the art for delivering electrical stimulating pulses to selected body tissue and typically comprise an implantable pulse generator (IPG) for generating the stimulating pulses under prescribed conditions and at least one lead bearing a stimulation electrode for delivering the stimulating pulses to the selected tissue. For example, cardiac pacemakers and implantable cardioverter/defibrillators (ICDs) have been developed for maintaining a desired heart rate during episodes of bradycardia and for applying cardioversion or defibrillation therapies to the heart upon detection of serious arrhythmias, respectively. Other nerve, brain, muscle and organ tissue stimulating medical devices are also known for treating a variety of conditions.

The earliest implantable pacemaker IPGs employed very simple analog circuit oscillators formed by discrete transistors and other circuit components and were very short-lived and electrically inefficient. The incorporation of digital discrete ICs for logic and memory functions arrayed on circuit substrates and forms of hybrid circuits enabled higher electrical efficiency and set the stage for the development of more sophisticated operating functions, programmability of operating modes and parameters, data storage and telemetry of stored data as embodied in the MEDTRONIC® SPECTRAX® pacemaker IPGs.

Over the past 30 years, such IMDs have evolved, from relatively bulky, crude, and short-lived devices providing simple stimulation therapies and monitoring functions to complex, long-lived, and miniaturized IMDs providing a wide variety of pacing, cardioversion and defibrillation therapies and/or monitoring functions. Numerous other programmable functions have been incorporated including enhanced capacity to detect and discriminate cardiac arrhythmias, to store data and to uplink telemetry data related to arrhythmia episodes and applied therapies (if any). Moreover, the capability of interrogating stored device data and real time telemetry of physiologic data, e.g. the real time cardiac EGM and blood pressure and the like, have been incorporated into such IMDs.

Over the same time period, numerous improvements have been made in leads and sensors that are attached to the IMDs which provide for more reliable sensing of physiologic signals and delivery of therapies in therapy delivery IMDs. For example, improved pacing and sensing leads and cardioversion/defibrillation leads and electrodes that have enabled sensing the atrial and ventricular EGM and the delivery of pacing and cardioversion/defibrillation energy at specific selected upper and lower heart chambers. These improvements have led to dramatic reductions in the delivered pacing and shock energy required to capture and cardiovert or defibrillate a heart chamber, respectively. Moreover, in ICD IPGs, the high voltage output circuitry has been improved in many respects to provide monophasic, bi-phasic, or multi-phase cardioversion/defibrillation shock or pulse waveforms that are efficacious, sometimes with particular combinations of cardioversion/defibrillation electrodes, in lowering the required shock energy to cardiovert or defibrillate the heart.

It is widely understood that such IMDs need to be small enough to be comfortably implanted subcutaneously without being unduly uncomfortable to the patient or cosmetically apparent and must be energy efficient enough to function reliably for many years. Throughout the course of development of these improvements, successive generations of such IMDs have incorporated improved, miniaturized electronic ICs and hybrid circuitry that are powered by long-lived, low current output, low voltage batteries. Most recently, a wide number of IMD system architectures have been developed that incorporate custom microcomputers comprising a microprocessor, RAM and ROM and related elements of a typical microcomputer and other control logic, memory and signal processing circuitry. Such microcomputer based system architectures typically are embodied in two or more ICs that are mounted to a substrate and electrically coupled together.

Improvements in such ICs has enabled the increased capability to store greater and greater amounts of data in IMD memory about the IMD itself, its implantation and history of operation, its programmed operating modes and parameter values, and data collected by the IMD and stored in internal memory. Such stored data includes device specific data that is either stored by the manufacturer, stored by the physician, or is accumulated by the IMD following a prescribed data collection operating routine. The data stored at manufacture can include device identification by model, serial number and date of manufacture and device specifications. Historic data is entered by the physician through use of an external programmer to downlink telemeter data to be stored in IMD memory, e.g., patient identification, identification of associated devices, e.g., sensors or leads or the like, coupled with the IMD at implant, operating modes and parameters programmed at specific follow-up dates, etc. The IMDs also monitor device states and conditions, e.g., battery voltage and lead impedance and provide uplink telemetry of such data when interrogated. Such IMDs have also been designed with memory capacity to store a great deal of physiologic data collected either continuously or upon satisfaction of data storage criteria. In therapy delivery IMDs, such data includes physiologic data related to the detection of a physiologic condition requiring delivery of a therapy, the therapy that was delivered, and the response to the delivered therapy.

For example, implantable physiologic monitors, e.g. the MEDTRONIC® Chronicle™ implantable hemodynamic monitor can store cardiac blood pressure data that for later uplink telemetry to an external programmer receiver in order to monitor the cardiac function of patients suffering from heart failure. The MEDTRONIC® Reveal™ insertable loop recorder is a form of implantable monitor that is intended to be implanted subcutaneously and has a pair of sense electrodes spaced apart on the device housing that are used to pick up the cardiac far field EGM which in this case is also characterized as a "subcutaeous ECG". The Reveal™ insertable loop recorder samples and records one or more segment (depending on the programmed operating mode) of such far field EGM or subcutaneous ECG signals when the patient feels the effects of an arrhythmic episode and activates the recording function by applying a magnet over the site of implantation. For example, the storage of a programmable length segment of the EGM can be initiated when the patient feels faint due to a bradycardia or tachycardia or feels the palpitations that accompany certain tachycardias. The memory capacity is limited, and so the segments of such EGM episode data that are stored in memory can be written over with new EGM episode data when the patient triggers storage and the memory is full. The most recently stored segment or segments of episode data is transmitted via an uplink telemetry transmission to an external programmer when a memory interrogation telemetry session is initiated by the physician or medical care provider using the programmer. Aspects of the Reveal™ insertable loop recorder are disclosed in commonly assigned PCT publication WO98/02209.

A great deal of data storage capacity has also been incorporated into cardiac pacemaker IPGs and ICD IPGs. The MEDTRONIC® family of Thera® multi-programmable single and dual chamber pacemaker IPGs provide for manufacturing, physician entered, and episodic EGM data storage of the types listed above for uplink telemetry to a MEDTRONIC® Model 9790C external programmer, for example. The MEDTRONIC® GEM 7227 single chamber or GEM DR 7271 dual chamber ICD IPGs are also programmable in operating modes and parameter values and store similar data that is interrogatable employing the MEDTRONIC® Model 9790C external programmer, for example. These ICD IPGs also provide for the uplink telemetry of data related to battery condition, lead impedance, high voltage (HV) capacitor charging time and charge energy, EGM data preceding and following the most recently detected tachyarrhythmia episode, the most recently delivered cardioversion/defibrillation therapy, and episode log historic data related to detections of tachyarrhythmia episodes and therapies delivered or aborted. A number of counters and timers accumulate episodic data related to heart rate, detected arrhythmias, successful and unsuccessful delivered therapies, etc. Memory capacity is provided in the single chamber and dual chamber ICD IPGs for storing digitized EGM data of one or more tachyarrhythmia detection episodes having programmable episode length times.

The EGM episode data and other data stored in such IMDs (herein referred to as IMD data) is intended to be encoded and telemetered out in an uplink telemetry transmission to an external medical device, commonly referred to as a programmer, in response to an interrogation command received from the programmer in a downlink telemetry transmission. Many types of RF telemetry systems have been or currently are used for uplink and downlink telemetry.

An example of a pulse interval modulation (PIM) telemetry system used for transmitting analog and digital data, individually and serially, from an implanted pacemaker IPG to a remote programmer is disclosed in U.S. Pat. No. 4,556,063, incorporated herein by reference. A further example of a pacemaker programmer for use with programmable cardiac pacemakers having RF telemetry capabilities is disclosed in U.S. Pat. No. 4,550,370, incorporated herein by reference. A further example of a pulse width modulation (PWM) telemetry system for transmitting binary "1" and "0" indicating pulse widths from an implanted cardiac pacemaker to an external programmer is described in U.S. Pat. No. 4,571,589, incorporated herein by reference.

An extensive description of the historical development of telemetry transmission formats and systems for both uplink telemetry of data from the implanted medical device to an external telemetry receiver and programmer and for downlink transmission of programming and telemetry trigger commands is set forth in the above-referenced '851 application. Commonly assigned U.S. Pat. No. 5,127,404 is among the first of a group of commonly assigned patents that disclose frame based, pulse position modulated (PPM), IMD data formatting for uplink telemetry transmission. This frame based, uplink telemetry format and system are incorporated into MEDTRONIC® Model 9760, 9766, 9770, and 9790C programmers.

The uplink telemetry RF pulses generated by the frame based, PPM telemetry transmitter are generally constant in pulse width. A fixed trigger or telemetry clock pulse is applied to the implanted device antenna circuit which momentarily couples battery voltage to the antenna L-C circuit. The L-C circuit responds by "ringing", generating a burst of damped sinusoidal, decaying amplitude RF cycles at the RF frequency, typically 175 kHz constituting the uplink telemetry RF pulse. The L-C time constant requires a minimum separation between telemetry clock pulses to ensure that the damped sinusoidal RF burst cycle amplitudes have decayed to baseline to ensure that successive RF pulses, and the PPM spacing between them, can be decoded in the telemetry receiver. The downlink telemetry RF pulses are generated in somewhat the same manner and share the same general characteristics.

The IMD data stored in the IMD memory registers is formatted as taught in the commonly assigned '404 patent and transmitted in an uplink telemetry transmission in response to a downlink telemetry interrogation command transmitted by the external programmer. The frame based, PPM telemetry system increases the data transmission rate significantly over the simple bit stream telemetry transmission schemes using either PWM or PPM or PIM to distinguish a "1" from a "0" while diminishing consumption of battery current. A great deal of data may be encoded in a single telemetry frame and transmitted within the telemetry frame period defined by a discrete number of internal clock cycles. However, the L-C time constant and attendant minimum separation distance required between the IMD and external programmer antennas does limit the telemetry frame defining telemetry clock frequency. Moreover, in a "noisy" environment, stray electrical signals can be picked up by the RF head antenna and can corrupt the uplink telemetered data that is demodulated and decoded in the external programmer receiver. Slight movements of the programming head over the site of implantation of the IMD can also introduce noise or cause signal loss or drop out during an uplink telemetry transmission.

The above-incorporated '404 patent and a number of other IMD telemetry patents disclose methods and apparatus for minimizing the corruption of data transmitted from the IMD to the external programmer due to such noise and signal loss. In addition, error detection schemes are disclosed that are used in order to ensure that any such corruption of the data that occurs during or because of a faulty uplink telemetry transmission is not mistaken as accurate data stored in the IMD. A serial CRC encoder within the frame formatting hardware of the IMD as shown in the above-incorporated '404 patent. The CRC encoder operates to calculate and append a CRC to a telemetry packet comprising at least two or more frames of uplink telemetered data as described in the above-incorporated '404 patent, for example, and a number of other commonly assigned telemetry patents. The use of telemetry CRC is also described in further U.S. Pat. Nos. 4,562,841 and 5,342,408, incorporated herein by reference. The calculation of a telemetry CRC for uplink and downlink telemetry transmission and error checking of telemetry packets comprising a plurality of telemetry data frames is disclosed in the '408 patent.

During uplink telemetry transmissions, the external programmer that receives the uplink telemetry transmission recalculates a CRC and compares it to the uplink telemetered, internally calculated, CRC to determine if an error in uplink telemetry transmission or reception has occurred. If an error is determined, the external programmer can command the IMD to repeat the transmission. Typically, the external programmer performs these functions in a software algorithm since power conservation and memory capacity are not of concern in such external medical devices.

Similar error checking functions are incorporated in wholly external medical telemetry systems that communicate and transmit data between externally worn patient monitors and a central station as described, for example, in U.S. Pat. Nos. 5,307,817, 5,558,638, 5,748,103 and 5,767,791, all incorporated herein by reference.

While these telemetry CRC functions are useful in eliminating mistaken acceptance of data corrupted in the course of the uplink telemetry transmission, it cannot correct or account for errors in or corruption of data stored in IMD memory prior to its interrogation, retrieval and formatting for uplink telemetry transmission. The above presented listing of storage capabilities is illustrative of the increased complexity and capacity of such IMDs. The ability to store ever increasing amounts and types of data depends on continuing improvements in the memory, typically RAM, which increase data storage capacity in a given IC die size and decrease energy requirements for reading and writing such data. However, as memory density increases, the probability that "soft" errors occur increases. Soft errors occur when a given memory cell spontaneously changes state from "1" as initially written to "0" or vice versa. "Hard" errors occur when a given memory cell cannot be written to change state, and such cells exhibiting hard errors can be detected during a data storage write operation and bypassed in favor of a good cell. Currently, there is no provision for determining or accounting for soft errors in data cells of IMD memory employed for the storage of such IMD data, and the likelihood that at least some data that could be of critical importance to the well being of the patient in which the IMD is implanted will become corrupted is increasing as memory is increased.

Moreover, if such IMD data within a data block is corrupted, it is not easy to determine just which data block is corrupted and where the defective byte or bytes of data are located in the data block. An error checking scheme is disclosed in U.S. Pat. No. 5,607,458 which involves providing a parity bit for every 8-bit data word stored in RAM or ROM that is periodically checked by a watchdog circuit.

It is a principal object of the present invention to overcome these deficiencies in the storage and maintenance of data in memory of an IMD.

SUMMARY OF THE INVENTION

In accordance the present invention, these problems are addressed by calculating and appending an error code to a block or blocks of IMD data as the IMD data are moved and/or read by a block mover/reader in a block move or read operation within an IMD so that data corruption can be detected.

In accordance with one aspect of the invention, these problems are addressed by calculating and appending a data CRC to a block or blocks of IMD data as the IMD data are moved and/or read by a block mover/reader in a block move or read operation within an IMD so that data corruption can be detected.

In accordance with a further aspect of the present invention, these problems are addressed by calculating and appending a syndrome value to a block or blocks of IMD data that are moved and/or read by a block mover/reader in a block move or read operation within an IMD so that the location of the data corruption within the data block or blocks can be detected.

The invention is preferably realized in a method or apparatus for calculating and appending an error code to block(s) of data stored in memory in an IMD when the block(s) of IMD data are initially moved between a data source, e.g., a temporary register or buffer where a data value is calculated, and a destination memory register.

Additionally, the stored error code is employed, at other times during a block move and/or read operation, by re-reading the IMD data, re-calculating the error code as the IMD data is read, comparing the re-calculated error code to the stored error code, and employing the results of the comparison to discard or tag IMD data block corrupted since the time that the associated error code was calculated and stored. In this case, the error code is preferably the data CRC calculated by CRC calculation logic from one or more blocks of IMD data bytes or words as the data bytes are read and accumulated in a CRC register. The contents of the CRC register are stored or used as a re-calculated CRC in the comparison to a previously calculated and stored CRC.

Optionally, a syndrome value is also calculated by syndrome calculation logic and accumulated in a syndrome register as each byte of data of the data block(s) is read. The syndrome value is stored in memory in association with the block(s) of IMD data upon their storage in IMD memory. At a later time, during a block move and/or read operation, the IMD data is re-read and the syndrome value is re-calculated and accumulated in the syndrome register. When all bytes of the block(s) of IMD data are re-read, the stored syndrome value is read into the syndrome register. If the syndrome values are the same, the resultant syndrome register value will be reduced to a known quantity, e.g., all "zeros". If an error has occurred in a data bit among the re-read data block(s), then the resultant syndrome value will be a binary number that points to the erroneous bit among the data bytes of the data block(s).

The calculation and application of the data CRC and optionally the syndrome value accompanies one of the following IMD functions:

(1) Accompanying movement of a block of sampled physiologic data from FIFO memory registers to permanent memory registers intended to be retained for uplink telemetry to an external medical device or programmer at a later time;

(2) Accompanying storage of device operating data related to specific device operations, e.g., detection of a tachyarrhythmia episode and delivery of an anti-tachyarrhythmia therapy; and (3) Accompanying storage of patient identification, implant data, and programmed operating mode and parameter values transmitted to the IMD from the external programmer during initial implantation and patient follow-up.

The data CRC (and optionally the syndrome value) for one or more sequential data blocks of a plurality of data bytes or words is calculated during a block read operation conducted by a block mover/reader implemented in hardware. Each data byte of the data block(s) is read into a parallel data register of the block mover/reader in a first, data read, clock cycle and the CRC and syndrome value in CRC and syndrome registers of the block mover/reader are updated during that clock cycle. When all data bytes of the data block(s) are read (and optionally moved as described below), the data CRC and optionally the syndrome value are stored as the associated data CRC and optional syndrome value or are used for comparison with a stored data CRC and optional syndrome value associated with the data block(s) in the comparison operation to determine if the data block(s) is corrupted.

In the block move operation, each data byte or word in the block mover data register is read in a first clock cycle and then moved to a destination register of IMD memory in a second clock cycle (for simplicity, the sequential read and move operations are usually referred to herein only as a block move operation). The data CRC and optionally the syndrome value accumulate in the CRC and syndrome registers as all data bytes of the data block(s) are read. When the last data byte or word of the data block(s) is sequentially read and moved, the accumulated data CRC and syndrome value are either stored as the associated data CRC and optional syndrome value or are used for comparison with a previously stored data CRC and optional syndrome value associated with the data block(s) in the comparison operation to determine if the data block(s) is corrupted.

The data read/move operations and the calculations of the CRC and optional syndrome value are advantageously conducted very quickly (two clock cycles per data byte or word) and at low current consumption. The microprocessor in the IMD CPU is not employed and interrupts are disabled in the data read/move operations, saving operating current. The source and destination registers of the data bytes of the data block(s) are accessed by the DMA controller of the IMD operating system reading source and destination registers in the block mover/reader.

Because there are no restrictions on the source and destination memory blocks, a memory block can be filled by setting the first byte of the memory block to the fill value and then setting the source address to the beginning of the memory block, and the destination to the one more than the beginning of the memory block.

The data CRC of a data block can be computed without transferring the data by using the read only mode because the CRC is computed on the read portion of a two clock cycle data transfer. Between data block transfers, the CRC and syndrome values in the CRC and syndrome registers of the block mover/reader remain unchanged. Therefore, the CRC and syndrome values can be computed across a sequence of data blocks that are larger than the maximum data block length or word count that can be accommodated by the data block mover/reader. Alternatively, the CRC and syndrome values in the CRC and syndrome registers of the block mover/reader can be initialized to known binary numbers prior to a given block read or move operation.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

The foregoing features and advantages of the invention will become apparent to those skilled in the art from the following detailed description of a preferred embodiment, especially when considered in conjunction with the accompanying drawings in which:

FIG. 4(A) is a schematic diagram of an IMD data block of N data bytes and the associated CRC and syndrome value calculated therefrom;

FIG. 4(B) is a schematic diagram of a series of X IMD data blocks each formed of one or more data byte and the associated CRC and syndrome value calculated therefrom;

DETAILED DESCRIPTION OF THE PREFERRED EMBODIMENTS OF THE INVENTION

The present invention can be implemented in any IMD that employs data storage. The present invention will be described in relation to an ICD IPG operating system design, but it is not intended that the invention be limited to that particular application when it can be advantageously implemented in other ICD IPG operating systems and in operating systems of other therapy delivery or monitor IMDs.

Such ICD IPGs typically are formed having a housing that is hermetically sealed and, therefore, is impervious to body fluids, and a connector header for making electrical and mechanical connection with one or more leads bearing pacing, sensing and cardioversion/defibrillation electrodes adapted to be located in or around selected chambers of the heart. The housing is formed of a suitable, body-compatible material approved for medical use, such as titanium and is shaped physiologically so as to avoid sharp edges which might lead to tissue necrosis following implantation. Typically, the housing is formed having major opposed or parallel surfaces joined together by sides enclosing an interior housing chamber or cavity and having electrical feed-throughs extending therethrough and into the connector header. The housing cavity receives the battery(s) and the high voltage (HV) and low voltage (LV) electronic circuitry which can comprise ICs, hybrid circuits and discrete components, e.g., but not limited to, the step-up transformer and the high voltage output capacitor(s). Although, there is no particular preferred embodiment of such an ICD, FIGS. 1 and 2 depict one form of such an ICD in which the present invention can be advantageously implemented.

Figure 1:
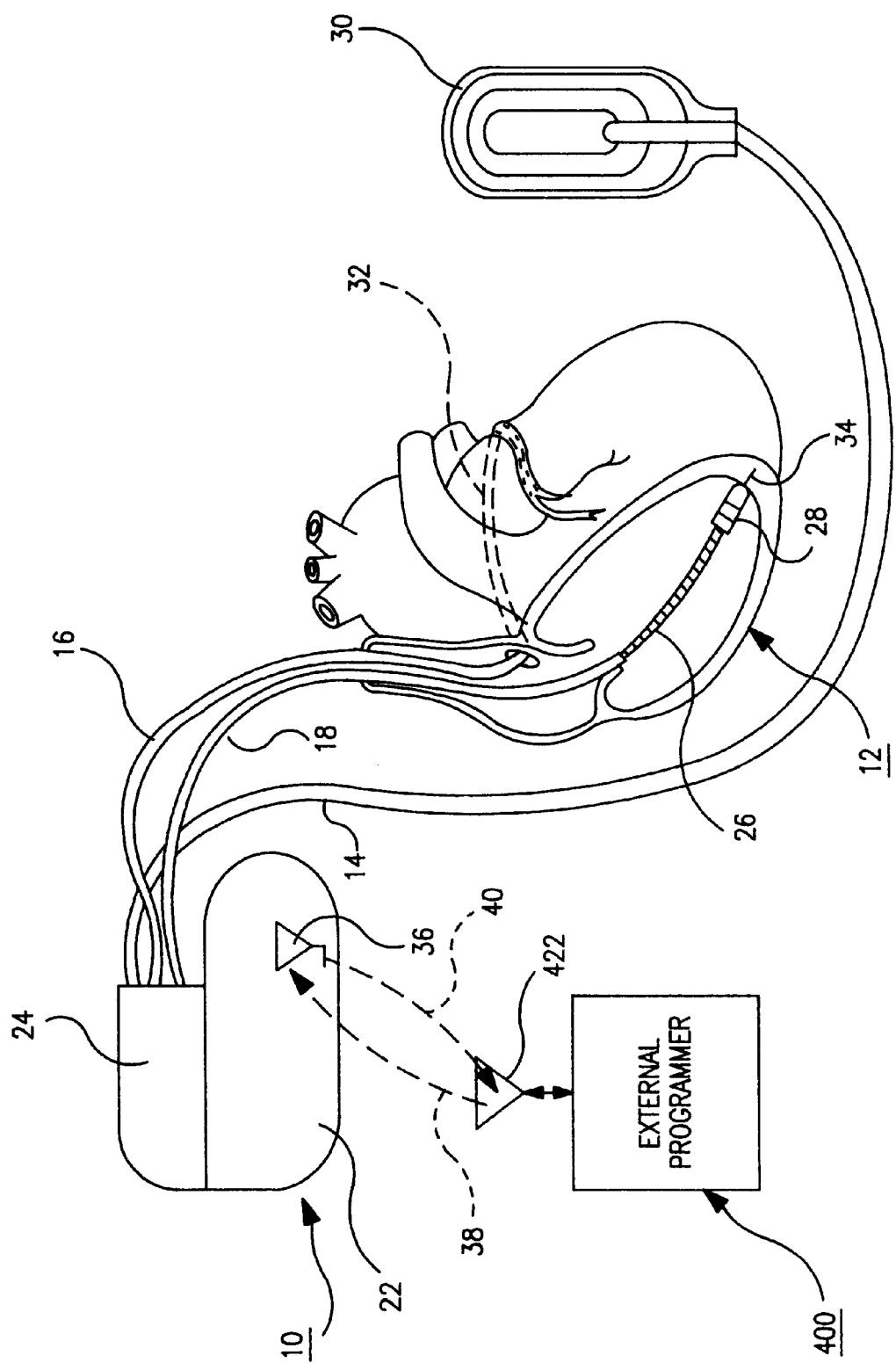
FIG. 1 illustrates the physical components of an ICD IPG and lead system extending to the heart illustrative of a type of IMD in which the block mover/reader of the present invention may be advantageously practiced.
Figure 2:
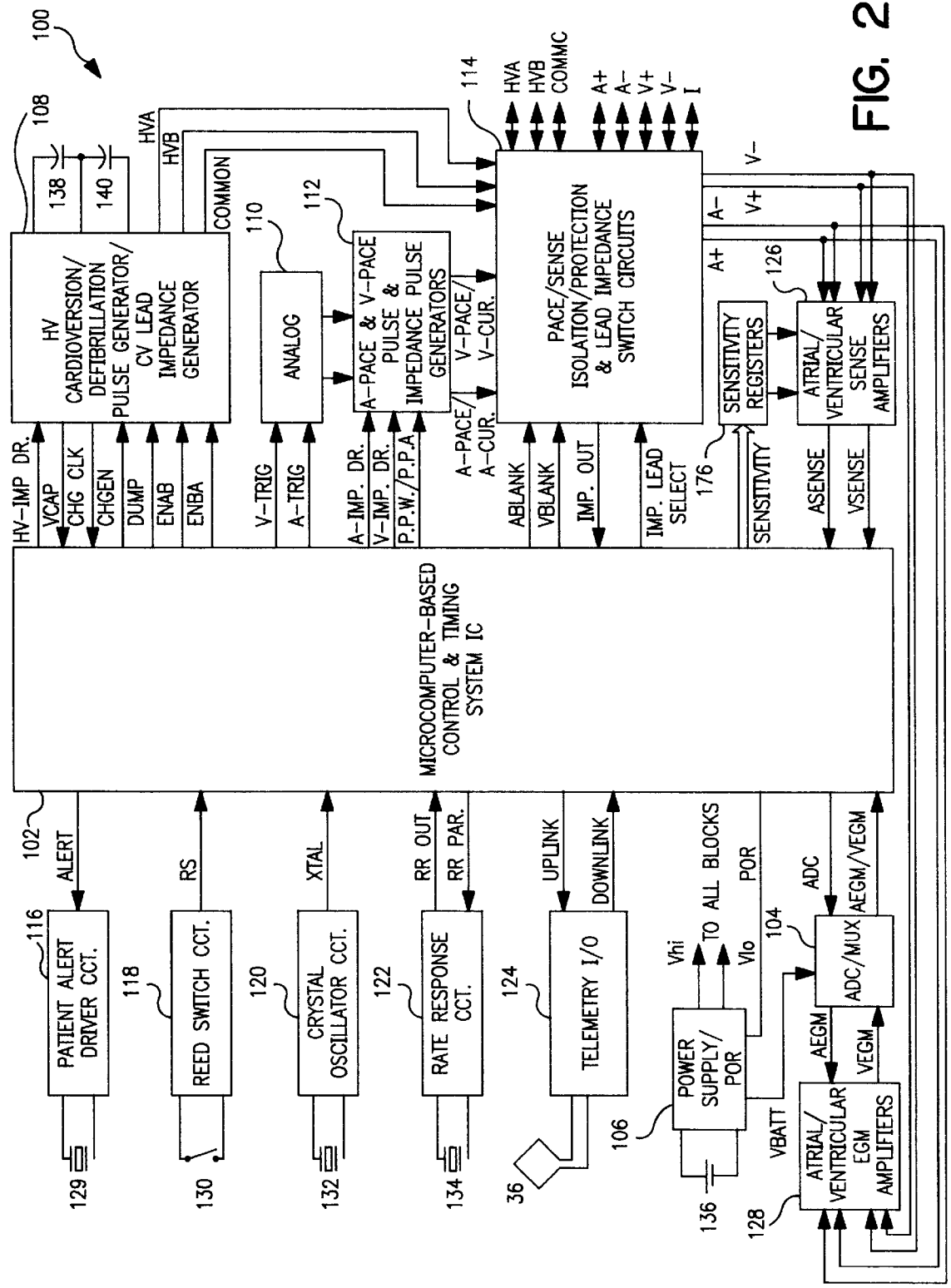
FIG. 2 is a functional block diagram of an ICD operating system of the ICD IPG of FIG. 1 in which the block mover/reader of the present invention may be advantageously practiced.

In FIG. 1, an ICD IPG 10 and associated 14, 16 and 18 are illustrated in relation to a patient's heart 12 as in FIG. 1 of commonly assigned U.S. Pat. No. 5,265,588, incorporated herein by reference in its entirety, in relation to an external programmer 400 and external programmer telemetry antenna 422. Over the past 20 years, ICD IPGs have evolved, as described in some detail in, from relatively bulky, crude, and short-lived IPGs simply providing high energy defibrillation shocks to complex, long-lived, and miniaturized IPGs providing a wide variety of pacing, cardioversion and defibrillation therapies. Numerous other programmable functions have been incorporated including enhanced capacity to detect and discriminate cardiac arrhythmias, data storage and uplink telemetry of data related to arrhythmia episodes and applied therapies, provision of staged therapies appropriate to the detected arrhythmia, for example. At the of staged therapies appropriate to the detected arrhythmia, for example. At the same time, numerous improvements have been made in cardioversion defibrillation leads and electrodes that have enabled the cardioversion defibrillation energy to be precisely delivered about selected upper and lower heart chambers and thereby dramatically reducing the delivered shock energy required to cardiovert or defibrillate the heart chamber. The IPG 10 comprises the hermetically sealed, metallic housing 22 and a multi-lumen connector header 24 which contains separate connector blocks and ports for receiving and electrically and mechanically attaching the proximal connector ends of the leads 14, 16 and 18. The feed-throughs (not shown) extend from the connector blocks (not shown) within the connector header 24 and the internal high voltage and low voltage circuitry within the housing 22 in a manner well known in the art.

The cardioversion/defibrillation leads 14, 16 and 18 bear relatively large surface area cardioversion/defibrillation electrodes 30, 32 and 26, respectively that are located in, on or about the heart 12. Cardioversion/defibrillation lead 14 extends subcutaneously and terminates distally in a subcutaneous electrode 30, which is intended to be mounted subcutaneously in the region of the left chest Cardioversion/defibrillation lead 16 extends transvenously and terminates distally in an elongated coil CS electrode 32 which is located in the coronary sinus and great vein region of the heart 12 and extends around the heart from a point within the opening of the coronary sinus to a point in the vicinity of the left atrial appendage. Ventricular cardioversion/defibrillation lead 18 extends transvenously and is provided with an elongated, exposed coil, electrode 26 which is located in the right ventricular chamber of the heart 12. Cardioversion/defibrillation shocks can be applied between selected cardioversion/defibrillation electrodes.

As illustrated, it is anticipated that the right ventricular cardioversion defibrillation electrode 26 will serve as the common electrode during sequential and simultaneous pulse or shock, multiple electrode defibrillation regimens. A number of cardioversion/defibrillation shock delivery operating modes are programmable and can depend upon the selection and location of the cardioversion/defibrillation leads and electrodes to provide differing shock waveforms and cardioversion/defibrillation pathways. For example, a simultaneous shock defibrillation regimen can be programmed, wherein shocks are simultaneously delivered between cardioversion/defibrillation electrodes 26 and 30 and between cardioversion/defibrillation electrodes 26 and 32. During sequential, bi-phasic, shock defibrillation, it is envisioned that cardioversion/defibrillation shocks would be delivered sequentially between cardioversion/defibrillation electrodes 30 and 26 and between coronary sinus cardioversion/defibrillation electrode 32 and right ventricular cardioversion/defibrillation electrode 26. Single polarity, two electrode, defibrillation shock regimens may be also provided, typically between right ventricular cardioversion/defibrillation electrode 26 and coronary sinus cardioversion/defibrillation electrode 32. Alternatively, single polarity shocks may be delivered between cardioversion/defibrillation electrodes 28 and 30. The particular interconnection of the cardioversion/defibrillation electrodes to the ICD IPG 10 will depend somewhat on which specific cardioversion/defibrillation shock regimen is employed.

The ICD IPG 10 preferably further incorporates atrial and/or ventricular EGM sensing capabilities for detecting atrial and ventricular sensed events (P-waves and R-waves) and for storing or uplink telemetry transmitting atrial and/or ventricular EGM segments. Ventricular lead 18 also includes a ventricular pace/sense electrode 34 which can take the form of a helical coil which is screwed into the myocardial tissue of the right ventricle or a tined lead passively fixed in the right ventricular apex. Lead 18 may also include an additional pace/sense electrode 28 for near field ventricular EGM sensing or a surface electrode on the IPG 10 may be paired with the helical coil electrode 26 for far field ventricular EGM sensing.

In the system illustrated in FIG. 1, the ventricular pace/sense electrodes 28 and 34 are coupled with a ventricular sense amplifier employed to sense R-waves for determination of heart rate. Ventricular cardiac pacing pulses are delivered between the ventricular pace/sense electrodes 28 and 34 in a WI pacing mode or a WIR pacing mode when the patient's intrinsic ventricular heart rate falls below a programmable lower rate or activity related physiologic rate, respectively. Additional near field and/or far field atrial EGM sensing and atrial pacing capabilities can be provided using atrial pace/sense electrode pairs on the atrial lead 16 and/or the IPG 10 to provide for DDD or DDDR pacing modes to restore atrial and ventricular synchrony when required. As noted below, atrial and/or ventricular antitachycardia overdrive and burst pacing therapies can also be applied between the atrial and/or ventricular pace/sense electrode pairs. A more detailed description of the leads illustrated can be found in commonly assigned U.S. Pat. No. 4,932,407, incorporated herein by reference in its entirety. The invention is believed workable in the context of multiple lead and electrode systems appropriate for the monitoring and treatment of the patient's cardiac arrhythmias.

The programming of ICD operating modes and parameters or the interrogation of data stored in the ICD IPG 10 or the initiation of uplink telemetry transmission of the cardiac EGM is accomplished or initiated via programming or interrogation commands transmitted in a downlink telemetry transmission 38 by programmer 400 from the external telemetry antenna 422 to the ICD telemetry antenna 36. The ICD IPG telemetry system decodes the commands in the downlink telemetry transmission 38, retrieves and formats the responsive data or cardiac EGM and conveys it to the external programmer 400 as an uplink telemetry transmission 38 in the manner described above, for example.

The ICD IPG 10 preferably comprises an ICD operating system that provides the operating modes and functions of the MEDTRONIC® GEM 7227 single chamber or GEM DR 7271 dual chamber ICD, IPGs that are programmable in operating mode and parameter values and interrogatable employing the MEDTRONIC® Model 9790C external programmer 400, for example. FIG. 2 is a functional block diagram illustrating such a dual chamber ICD operating system 100 that is merely exemplary of a variety of single chamber and dual chamber ICD systems having all or some of the capabilities described above in which the data block reading and moving operations of the present invention can be advantageously implemented.

The ICD system 100 includes one of more ICs typically mounted on one or more hybrid circuit, a PC board mounting a number of discrete components, and further large scale, discrete components. The heart of the ICD operating system is in hardware and software in the microcomputer based timing and control system IC 102 that is coupled with the other system blocks and further described in FIG. 3. Various depicted signal and control lines interconnecting these blocks, but not all are shown for simplicity of illustration and because they play no material role in the practice of the present invention.

The large scale, discrete, off-board, components include one or more batteries 136, HV output capacitors 138, 140, and housing mounted, patient alert sound transducers 129 and/or activity sensors 134. The discrete components mounted to the PC board include telemetry antenna 36, reed switch 130, crystal 132, a set of HV discrete components of the HV cardioversion/defibrillation output circuitry 108, and switching and protection circuit components of block 114. These discrete components are coupled to system IC 102 through other ICs and hybrid circuits incorporating the functional blocks 104–128 and 176 described further below. If the architecture of the above-incorporated '588 patent depicted in FIG. 3 thereof is employed, the depicted functional blocks and discrete components of FIG. 2 are arranged as part of one or two LV hybrid circuits, a HV hybrid circuit and a discrete component PC board. However, it will be understood that a single hybrid circuit could be employed that incorporates and supports all of the system ICs. Similar ICD systems to that depicted in FIG. 2 in which the present invention can be implemented are shown, for example, in U.S. Pat. Nos. 4,830,006, 4,693,253, 4,971,058, 5,312,441, and 5,827,326, all incorporated herein by reference in their entireties, for example.

The exemplary ICD operating system 100 of FIG. 2 is powered by the battery 136 coupled to power supplies in power source block 106 for developing regulated high and low voltage power supplies Vhi and Vlo that are supplied to selected ones of the other functional blocks. Preferably, battery 136 is a lithium silver vanadium battery that can be employed to provide HV capacitor charging current and that produces a voltage from about 3.2 volts when fresh to about 2.5 volts at specified end of service for a single chamber ICD and twice these values for a dual chamber ICD. Power supply 106 also includes a power-on-reset (POR) circuit that generates a POR signal initially when the battery 136 is connected with power supply 106 and any time that the voltage of battery 136 falls below a threshold voltage.

The crystal oscillator circuit 120 is coupled to dock crystal 132 and provides one or more system XTAL clock that is applied to the microcomputer-based control and timing system IC and distributed to other blocks of FIG. 2 as appropriate.

The telemetry I/O circuit 124 coupled with the IPG telemetry antenna 36 includes an uplink telemetry transmitter that receives formatted UPLINK signals for uplink transmission and a downlink telemetry receiver that receives and forwards DOWNLINK signals to telemetry I/O registers and control circuitry in system IC 102. The telemetry I/O circuit 124 is enabled to receive and decode downlink telemetry interrogation and programming commands when the reed switch circuit provides the RS signal upon closure of reed switch 130 by an external programming head magnetic field. Downlink telemetry RF signals ring an L-C tank circuit including the IPG telemetry antenna 36. Other pacing functions are also affected when a magnetic field closes the reed switch 130 and the RS signal is generated in a manner well known in the art.

The rate response circuit 122 is coupled to a physiologic activity sensor 134 which is preferably a transducer or accelerometer mounted to the IPG housing inner surface and provides activity correlated output signals to the rate response circuit 122 in a manner well known in the art. The output signal processing by the rate response circuit can be programmed in a number of ways known in the art.

The patient alert driver circuit 166 is coupled to a sound emitting transducer 129 which is mounted adjacent to the interior surface of the IPG housing and is powered to emit audible warning signals in high urgency and low urgency tones to alert the patient of events or conditions of concern warranting physician intervention. The warnings that can be programmed into operation or programmed "off" include pace/sense and CV/DEFIB lead impedance out of range (too high or too low), low battery voltage, excessive charge time for charging the HV capacitors, all therapies in a programmed group of therapies exhausted for a given episode, and an indication of the number of shocks delivered in an "episode".

Periodically, e.g., once a day, a lead impedance test is initiated to measure the impedance of all of the lead conductors and associated electrodes that are in use. Impedance measurement current is injected through the leads and between their electrodes while the impedance is measured in a manner described in commonly assigned U.S. Pat. No. 5,755,742, incorporated herein by reference, and employed in the above-described MEDTRONIC® GEM 7227 single chamber or GEM DR 7271 dual chamber ICD, IPGs. In FIG. 2, selected lead impedance switches are closed in the switch circuit block 114 for injecting current and measuring impedance by commands from the operating system IC 102. Impedance measurement current is applied to the leads selected for current injection through the closed switches in the switch circuit block 114 by impedance current generators in the HV output block 108 or the atrial and ventricular pacing output block 112. The low amplitude impedance current is generated and applied at a sub-threshold energy level insufficient to capture the heart or cause pain to the patient.

The atrial and ventricular sense amplifiers in block 126 are coupled to the A+, A− and V+, V− pacing leads through the pace/sense isolation/protection and lead impedance switch circuits. The atrial and ventricular sense amplifiers in block 126 each comprise a programmable gain, bandpass amplifier, a threshold setting circuit and a comparator for comparing the bandpass filtered atrial and ventricular cardiac signal amplitude to the threshold. The atrial and ventricular sense amplifiers thereby generate ASENSE and VSENSE signals, respectively, when their inputs are not blanked by blanking circuits in block 114 and the atrial and ventricular cardiac signal amplitudes exceed the respective atrial and ventricular thresholds. The sensitivity of each of the atrial and ventricular sense amplifiers is programmable in sensitivity registers 176.

The atrial and ventricular cardiac signals conducted through the A+, A– and V+, V– pacing leads are also applied to inputs of atrial and ventricular EGM amplifiers 128 which supply the amplified AEGM and VEGM signals to ADG/MUX 104. In the ADC/MUX 104, the AEGM and VEGM are continually sampled and digitized, and the digitized AEGM and VEGM are provided to RAM memory registers or buffers in system IC 102 for temporary storage on a FIFO basis. When a tachyarrhythmia episode is detected, the temporarily stored, digitized AEGM and VEGM values are shifted into memory registers. Then, succeeding digitized AEGM and VEGM values are also stored in memory registers to provide programmable length AEGM and VEGM strips preceding and following the detection of the arrhythmia and encompassing the delivery of the tachyarrhythmia therapies.

As noted below, data related to the delivered therapies is also stored in association with the AEGM and VEGM strips. Due to memory limitations, the stored AEGM and VEGM strip may be discarded and replaced each time a tachyarrhythmia is detected. However, historic episode logs are compiled and incremented in RAM in system IC 102 that provide the date, time, type of episode, cycle length, duration, and identify the last stored EGM strip. Other episode records stored in registers in RAM in system IC 102 are also maintained related to V—V intervals, numbers of single premature ventricular contractions (PVCs), runs of PVCs, tachyarrhythmias detected, therapies delivered, successful and unsuccessful therapies, etc.

The depicted HV cardioversion/defibrillation output circuit 108 of the type described in the above-incorporated '588 patent comprises a DC—DC converter and a HV output or discharge circuit for discharging the charge on the HV output capacitor bank 138 and 140 through the cardioversion/defibrillation leads and electrodes of FIG. 1. The DC—DC converter comprises a HV charging circuit, a discrete HV step-up transformer, and the HV output capacitor bank 138 and 140 coupled to the secondary transformer coils. This sub-system would be incorporated into the HV hybrid circuit and the PC board of the above-incorporated '588 patent architecture, if that architecture were followed. The charge on the HV output capacitor bank 138 and 140, in this case, is selectively discharged through combinations of the leads coupled with the cardioversion/defibrillation electrodes 26, 30 and 32 of FIG. 1 via HV switches in the switch circuit block 114 as described further below.

Figure 3:
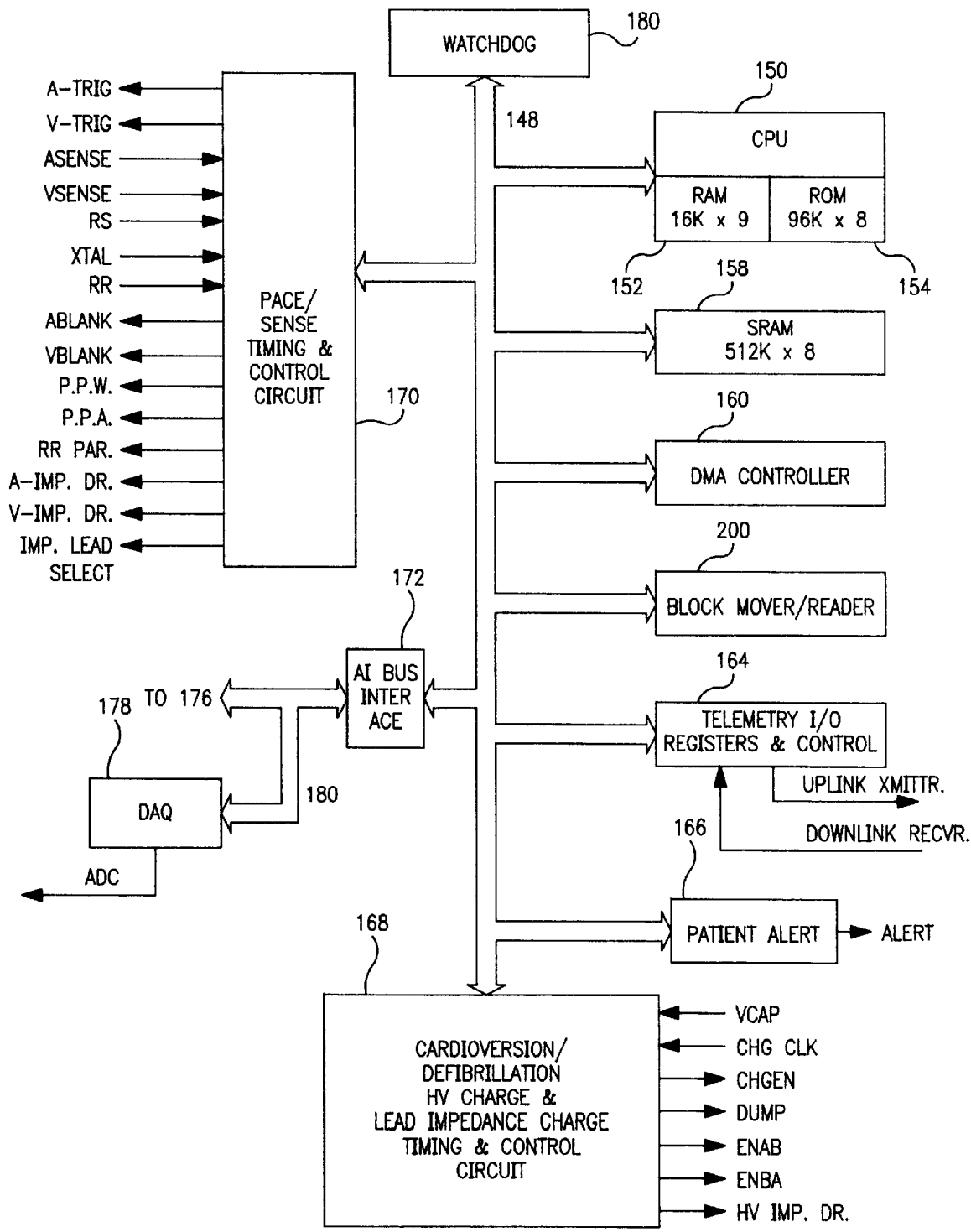
FIG. 3 is a functional block diagram of the microcomputer based control and timing system of FIG. 2 in which the block mover/reader of the present invention may be advantageously practiced.

The operating modes of the ICD operating system 100 are controlled by the microcomputer based control and timing system IC 102 depicted in FIG. 3 which receives the depicted signals from and provides signals and data to the blocks 104–128 and 176 of FIG. 2. The system IC 102 comprises the typical components of a microcomputer within CPU 150, further operating system control circuitry that is conveniently located with it. The functional blocks of system IC 102 are interconnected by a data/control bus 148 which schematically depicts all of the separate data buses, address buses and other control and signal lines and buses that may interconnect these blocks of system IC 102 (as well as certain blocks of FIG. 2) and which, for convenience is referred to as a "data/control" bus.

The microcomputer components include the microprocessor based CPU 150, the on-chip RAM 152 and on chip ROM 154, the larger capacity off-chip SRAM 158, and the DMA 160 interconnected via the data/control bus 148. The bidirectional data/control bus 148 and certain discrete interrupt and control lines (not shown) link an input/output interface of CPU 150 and input/output interfaces of the other depicted blocks of FIG. 3. These on-chip interfaces contain chip-select, address decoding and data bus logic as is typically employed with microprocessor peripherals. The bidirectional data/control bus 148 also interconnects the interfaces of the CPU 150 with the analog bus interface 172 for adjustable analog components and registers, e.g. the sensitivity registers 176 of FIG. 2.

The DMA controller 160 connected with data/control bus 148 operates in a manner well known in the art to provide for direct memory access to source and destination registers in SRAM 158, RAM 152 and ROM 154. The DMA controller 160 can be invoked without involving the microprocessor in CPU 150 in order to conserve battery voltage and to simplify data read and move operations.

The watchdog block 180 monitors the operation of the microprocessor in CPU 150 to ensure that it is operating properly. If the microprocessor is operating properly, it periodically polls the watchdog block 180 via data/control/bus 148 which responds by restarting a watchdog timer. If the microprocessor fails to poll the watchdog block 180 before the watchdog timer times out, the watchdog block 180 issues a processor fault signal on data/control bus 148. The watchdog block 180 also is interconnected with the POR circuit within power supply 106. If the POR circuit in power supply 106 detects power failure conditions, which might be temporary, it issues the POR signal to watchdog block 180. A backup operating mode is initiated in the pace/sense timing and control circuit 170 that effectively shuts down the CPU 150 and operates the IMD in a safe operating mode with nominal operating parameters if either a POR signal is generated or if the watchdog block 180 issues a processor fault signal. A warning may also be delivered via patient alert driver circuit 166 that informs the patient to notify his/her health care provider.

The CPU 150 performs the logical operations directed by the program code in response to the interrupts and control signals provided on data/control bus 148. Operating system firmware is written into ROM 154, and programmed operating modes and parameters are typically written into registers of RAM 152 but can be written into registers of SRAM 158 or dedicated registers in pace/sense timing and control block 170. Typically, the program code that governs operation of the ICD system 100 is stored in ROM 154, and the operations are carried out following operating modes and parameters that are stored as operating system data in RAM 152. The operating mode and parameter data is programmable and interrogatable through downlink telemetry programming and interrogation operations via the telemetry I/O registers and control block 164. Such operating modes include a number of pacing, monitoring, tachyarrhythmia detection and therapy delivery modes and such operating parameters include pacing pulse width and/or amplitude, sense amplifier sensitivity, event data storage, arrhythmia detection parameters in a given mode, tachyarrhythmia therapy parameters, etc.

Data related to the ICD itself, the patient history, device history, tachyarrhythmia episodes, battery voltage, HV capacitor charging time, the last measured lead impedance and pace and sensed event logs and markers, and the like, that is currently interrogatable in the above-described MEDTRONIC® GEM 7227 single chamber or GEM DR 7271 dual chamber ICD, IPGs, is formatted in telemetry I/O registers and control block 164. The telemetry 110 registers and control block 164 is triggered to retrieve all such data via data/control bus 148 from registers in the circuits of the system IC 102, e.g., RAM 152, SRAM 158, ROM 154 and sensitivity registers 176. The telemetry I/O block 164 can also be commanded to uplink telemeter the real time, digitized AEGM and VEGM signals and the current battery voltage processed by ADC/MUX 104. The formatting includes the formatting of data frames in the manner described above-in the commonly assigned and incorporated telemetry patents, e.g., the '404 patent. The telemetry I/O registers and control block 164 also calculates, formats and uplink telemetry transmits telemetry CRC codes through the telemetry transmitter in telemetry I/O circuit 124 of FIG. 2.

The pace/sense timing and control 170 is required to provide inputs to and carry out many of the operations of the microcomputer 150 governing the atrial and ventricular pacing modes of operation which are preferably programmable. The rate response signal RR, the reed switch signal RS, the XTAL clock signal and the ASENSE and VSENSE signals generated in blocks of FIG. 2 are applied to the pace/sense timing and control 170. The depicted dual chamber pace/sense timing and control 170 times out synchronized atrial and ventricular pacing escape intervals that depend on the current operating mode and programmed lower and upper pacing rates. The atrial and ventricular pacing rates are allowed to vary between the lower and upper pacing rates in dependence upon the RR signal when physiologic pacing modes e.g., DDDR and DDIR modes, are programmed and not otherwise inhibited by excessive atrial heart rates. The pace/sense timing and control 170 also acts as an interface for applying the programmed rate response signal processing parameters to the rate response circuit 122.

In these operating modes, when the respective programmed escape interval timers time out, the pace/sense timing and control 170 generates the A-TRIG and/or V-TRIG pacing trigger signals that are applied to the analog rate limit circuit 110 of FIG. 2. The analog rate limit circuit 110 generates the AT and VT signals applied to the A-PACE and V-PACE pulse generators in pacing output block 112 of FIG. 2 after the atrial and ventricular rate limit timers time out in order to limit the atrial and ventricular pacing rates to safe upper pacing rates. The A-PACE and V-PACE pulse generators in pacing output block 112 respond to the AT and VT signals, respectively to generate the respective A-PACE and V-PACE pulses at pace pulse energies, that is, either or both of the pacing pulse width and amplitude. The pace pulse energies that are programmed by the physician and stored in RAM 152 and are applied from pace/sense timing and control 170 to the A-PACE and V-PACE pulse generators in pacing output block 112.

The pace/sense timing and control 170 also generates the A-BLANK blanking signals having programmed blanking intervals following any of the ASENSE, VSENSE, A-TRIG and V-TRIG signals and the V-BLANK blanking signals having programmed blanking intervals following both VSENSE and V-TRIG signals. The A-BLANK and V-BLANK signals are applied to the pace/sense isolation circuits in block 114 of FIG. 2 for rendering the atrial and ventricular sense amplifiers in block 126 of FIG. 2 inoperative for these programmed blanking intervals. Atrial and ventricular sense amplifier refractory periods are also timed out from these signals in the pace/sense timing and control 170 and employed to avoid resetting the respective atrial and ventricular escape intervals timed out therein if an ASENSE or VSENSE event falls within a respective refractory period to avoid inappropriate responses in a manner well known in the art.

The pace/sense timing and control 170 also implements certain operations of the tachyarrhythmia detection and classification algorithms carried out by the microcomputer 150 and stored in ROM 154 and in RAM 152. The intervals between and rates of ASENSE and VSENSE signals are tracked and compared to rate thresholds and other detection criteria to determine the onset of atrial tachycardias, fibrillation and flutter and ventricular tachycardias and fibrillation, respectively. The tachyarrhythmia detection criteria typically involves elevation of the spontaneous heart rate coupled with other onset, rate acceleration, stability criteria and various other criteria, e.g., morphology, as described, for example, in the above-incorporated '006, '058, and '441 patents, for example. The tachyarrhythmia detection criteria are specified in ROM 154, and programmable detection parameters are stored in RAM 152. The spontaneous heart rate is calculated in a heart rate timer maintained by the microcomputer 150, and other characteristics of the EGM are examined to determine whether or not a high rate EGM constitutes a normal sinus rhythm or a malignant tachyarrhythmia. Spontaneous heart rate and EGM width criterion are employed in the MEDTRONIC® GEM 7227 single chamber ICD IPG, and both the atrial and ventricular heart rates and EGMs are examined with information about conduction patterns, regularity and AV dissociation in the detection and classification algorithm employed in GEM DR 7271 dual chamber ICD, IPGs.

When a tachyarrhythmia episode is detected and classified, the appropriate programmed burst pacing therapy or synchronous cardioversion shock therapy or defibrillation shock therapy is delivered. A group of successively more aggressive therapies can be programmed to be delivered to convert a specified tachyarrhythmia that persists despite the delivery of the initial therapies of the group. The overdrive burst and adaptive pacing therapies are delivered via pace/sense timing and control 170. The cardioversion and defibrillation shock therapies are delivered through therapy delivery commands applied on data/control bus 148 to the cardioversion/defibrillation HV charge and lead impedance charge control circuit 168 which provides the appropriate commands to the HV cardioversion/defibrillation output circuit 108 which responds in the manner described above. Additionally, pacing regimens can also be programmed and timed out in the pace/sense timing and control 170 and generated in A-PACE and V-PACE pulse generators in pacing output block 112 for pacing for a programmed time following delivery of a CV/DEFIB shock therapy to capture the heart and establish a normal sinus rhythm.

If an atrial or ventricular tachycardia is detected by an atrial or ventricular tachycardia detection algorithm embodied in the microcomputer 150, and if an anti-tachycardia pacing therapy is prescribed to treat it, then the pace/sense timing and control circuit 170 is employed to trigger delivery of high rate A-PACE or V-PACE pacing pulses via A-PACE and V-PACE pulse generators in pacing output block 112. Again, the pacing pulse energy of each pacing pulse and the blanking periods following each pacing pulse are programmable. A number of other characteristics of high rate pacing pulse therapies are programmable establishing a fixed or adaptive (ramp) pacing rate, the number of pacing pulses in the burst, and the number of times that the burst can be supplied to terminate a single tachycardia episode. The ASENSE and VSENSE events are again analyzed following delivery of a burst pacing pulse therapy is delivered to determine whether the tachycardia has terminated. A fixed number of successively more aggressive burst pacing therapies can be programmed or cardioversion therapies can be programmed and delivered if a preceding therapy fails to terminate the tachycardia.

The cardioversion/defibrillation HV charge and lead impedance charge control circuit 168 receives commands on the data/control bus 148 from the microcomputer 150 to initiate delivery of a cardioversion/defibrillation shock therapy between the programmed CV/DEFIB electrodes when an atrial or ventricular fibrillation or flutter or a malignant high rate tachycardia is detected by the tachyarrhythmia detection and classification algorithm embodied in the microcomputer 150. The cardioversion/defibrillation HV charge and lead impedance output circuit 108 can also be commanded to test charge or reform the HV output capacitor bank 138, 140 or to provide the CV/DEFIB lead impedance test current. The cardioversion shock energy, waveform and discharge pathways described above with respect to FIG. I are programmed in RAM 152.

The functions and detailed circuit schematics of the circuitry of HV cardioversion/defibrillation output circuit 108 and cardioversion/defibrillation HV charge and lead impedance charge control circuit 168 are set forth in the above-incorporated '588 patent. As shown therein, the output capacitors 138 and 140 are coupled to secondary windings of a step-up transformer by means of diodes. The primary winding of the step-up transformer is coupled to HV charging circuitry. The HV charging circuitry is controlled by the CHDR signal supplied by control circuitry within system IC 102 when a malignant arrhythmia subject to cardioversion/defibrillation therapy is detected. The HV output capacitors 138 and 140 are charged by oscillations of the high frequency, HV transformer in the manner disclosed in detail in the above-incorporated '588 patent. The voltage across the output capacitors 138 and 140 is monitored and applied via the VCAP signal to the cardioversion/defibrillation HV charge and lead impedance charge control circuit 168 which detects the point when the VCAP signal level matches the programmed energy level of the cardioversion/defibrillation shock to be delivered. When that condition is satisfied, the cardioversion/defibrillation HV charge and lead impedance charge control circuit 168 terminates the CHDR signal and commences the operations to deliver the programmed monophasic or bi-phasic cardioversion/defibrillation shock to the selected cardioversion/defibrillation electrodes.

When a bi-phasic shock waveform is programmed, the cardioversion/defibrillation HV charge and lead impedance charge control circuit 168 provides the first control signal ENAB, the second control signal ENBA, and the DUMP signal which initiates discharge of the charge stored across the output capacitors 138 and 140. The cardioversion/defibrillation electrodes 26, 30 and 32 and associated lead conductors illustrated in FIG. 1 are coupled to the HV cardioversion/defibrillation output circuit 108 and are labeled as "COMMON", "HVA" and "HVB", respectively. During a logic signal on ENAB, a cardioversion/defibrillation shock is delivered between cardioversion/defibrillation electrodes 30 and 32. During a logic signal on ENBA, a cardioversion/defibrillation shock is delivered between cardioversion/defibrillation electrodes 32 and 26. However, other configurations are also possible. For example, subcutaneous cardioversion/defibrillation electrode 30 may be coupled to HVB electrode 32, to allow for a single polarity shock regimen to be delivered between electrodes 26 and 30/32. Moreover, the external surface of IPG housing 26 of FIG. 1 may be exposed and coupled as a remote subcutaneous cardioversion/defibrillation electrode replacing or augmenting the subcutaneous cardioversion/defibrillation electrode 30.

As noted earlier, the detection of a tachyarrhythmia triggers the storage of AEGM and/or VEGM data preceding and following satisfaction of the detection criteria and encompassing the delivery of any of the above-described therapies and triggers storage of therapy delivery data and increments various episode, therapy efficacy, aborted shock counts and capacitor charge times and dates related to the above which are maintained in memory registers in RAM 152 or SRAM 158. A considerable amount of other such IMD data is also accumulated independent of or incidentally related to a detected tachyarrhythmia episode. The above-described battery and lead impedance IMD data is also stored in such memory registers. Moreover, all of the above-described programmed operating modes and parameter values are maintained in such registers. All of this stored IMD data is subject to being interrogated and read out in a telemetry session initiated by the physician employing the external programmer 400 of FIG. 1 in a manner well known in the art.

As set forth at the outset, it is highly important that the data stored in such ICD IPGs and in other IMDs is not corrupted. In accordance with the present invention, an error code, e.g., a CRC check sum and optionally a syndrome value, is appended to IMD data blocks that are read or moved a data byte at a time from or between memory registers in the system IC 102. The block mover/reader 200 of FIG. 3 controls the reading and the movement of any data bytes between registers of RAM 152, SRAM 158 and registers in block mover/reader 162, in the telemetry I/O registers 164 and in the sensitivity registers 176 or read from registers of ROM 154.

The block mover/reader 200 comprises hardware that is used under the control of the CPU 150 to read or to read and move a block or several contiguous blocks of IMD data from a source address to a destination address on particular buses of data/control bus 148. The block mover/reader 200 also calculates the error code, e.g. a data CRC and syndrome value, for the data block or blocks when enabled to do so. The transfer and calculation operations are performed faster and with less energy consumption by the block mover/reader 200 than could otherwise be accomplished a software routine within the CPU 150. There are no restrictions on the types of data that can be transferred (i.e., read or moved). In this particular embodiment, the data block that is to be moved or read can be specified to contain from 1 to 256, for example, 8-bit bytes or words. All data bytes are read or moved within two clock cycles via an 8-bit data bus among data/control bus 148. All memory registers accessible via data buses in the data/control bus 148 are memory mapped, and so they can be the source or destination registers of a block read or move (even the block mover's registers, although that may not be wise).

In accordance with the present invention, during any block move or read operation, the block mover/reader 200 calculates the data block CRC and the syndrome value and stores them in specified destination registers. The destination registers can either be contiguous with the destination data registers or can be a particular set of dedicated CRC and syndrome memory registers. In the latter case, a table is maintained correlating the addresses of the data block with its CRC and syndrome value.

After a data block/move operation is initiated by the CPU 150, the block mover/reader 200 is in total control of the data/control bus 148 and the source and destination memory registers during the data transfers. The CPU 150 disables all interrupts that are otherwise applied to CPU 150 and then re-enables interrupts after the block move or read operation is completed. This is required to insure that an interrupt routine does not overwrite the block move registers prior to the execution of the block move or read operation. The block mover/reader 200 employs the DMA 160 to access the memory register addresses and accomplish a transfer operation from a source address to it and then to a destination address.

Periodically, the CPU 150 initiates a block read for error checking purposes. The CRC of the data block can be re-calculated for comparison to the previously calculated and stored CRC without actually moving the blocks of data. In this way, it can be determined if previously stored data has become corrupted, and the data can either be tagged as corrupted or can be discarded.

Typically, a CRC register and the syndrome register are initialized prior to calculating the CRC and syndrome values for a block of data that is read or moved. Optionally, the CRC register and syndrome register can be left not initialized after the first block of data in a sequence of such data blocks is read or moved in the block mover/reader 200. This allows CRC and syndrome calculation to take place for a sequence of data blocks.

Figure 5:
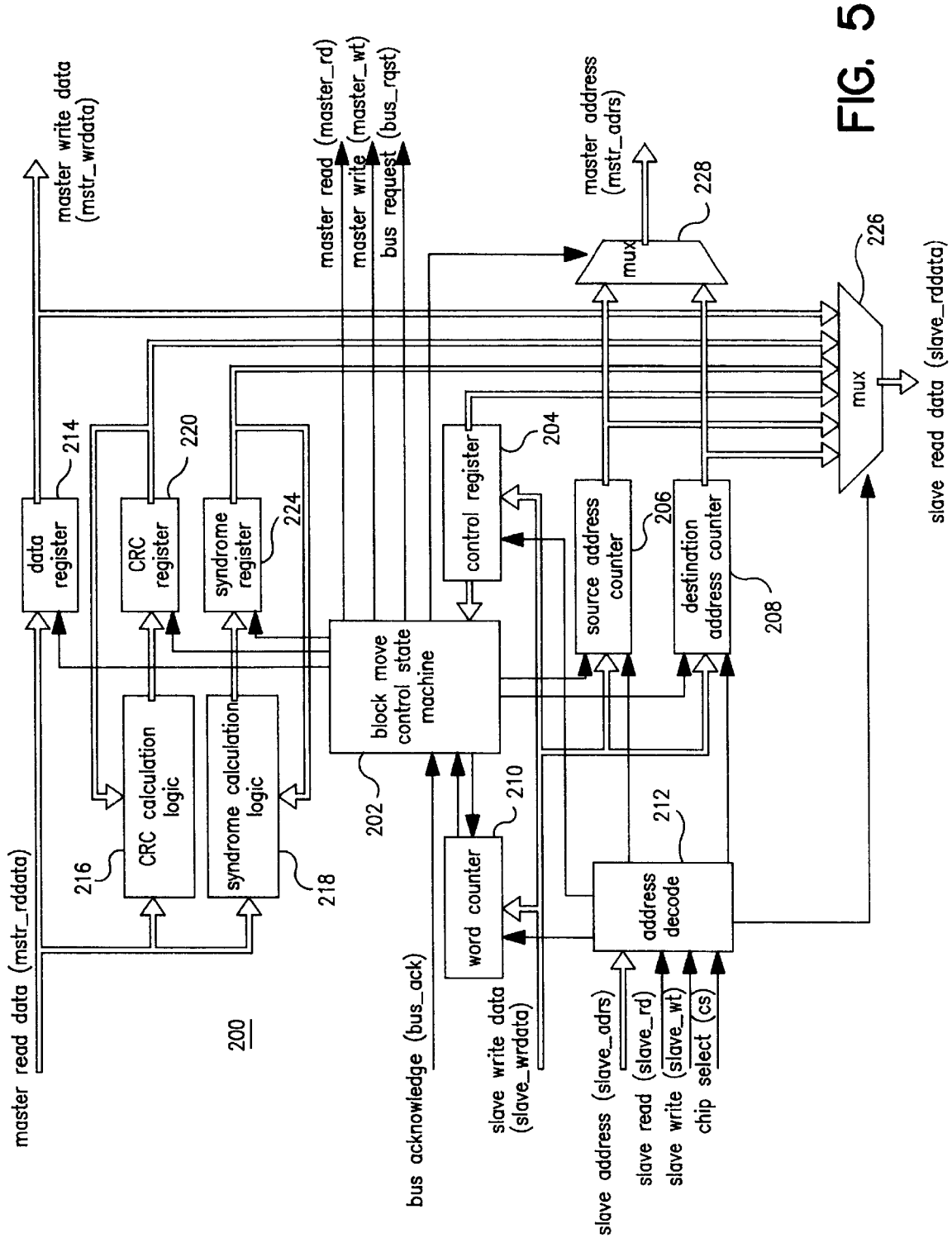
FIG. 5 is a block diagram of the block mover/reader of FIG. 3 for providing a hardware based calculation of a data CRC and optionally a syndrome value upon reading or moving a block of data resident in or moved from any buffers or data registers in the ICD operating system of FIGS. 2 and 3.

FIG. 5 depicts a block diagram of the block mover/reader 200 of FIG. 3 using the module I/O signal set for providing a hardware based calculation of the data CRC and the syndrome value upon reading or moving a block of data resident in or moved between any data registers in the ICD operating system 100 of FIGS. 2 and 3. The block mover/reader 200 is normally dormant and is awakened when CPU 150 commences a block transfer by issuing the slave interface signals.

The block mover/reader 200 can be used to derive error codes from one or more data blocks. FIG. 4(A) is a schematic diagram of an IMD data block of N data bytes and the associated CRC and syndrome value calculated from the N data blocks using the block mover/reader 200 as described further below. The value N can be between 1 and 256 8-bit bytes, and the CRC and syndrome values are 16 bits in length. FIG. 4(B) is a schematic diagram of a series of X IMD data blocks each formed of one or more 8-bit data byte and the associated CRC and syndrome value calculated from the X data blocks.

There are four main groups of signals or instructions or data which enter or leave the block mover/reader 200 via specified buses and control lines schematically included in data/control bus 148 of FIG. 3 and used by the CPU 150 or the DMA controller 160 or the block mover/reader as follows:

1) control—such as clocks and resets
2) bus request—
   signals input and output by the block mover 200 with DMA controller 160 to gain access to the control/data bus 148 to perform DMA transfers
3) slave interface—
   signals used/provided by the CPU 150 to read and write block mover registers 4) master interface—
   signals and data used/provided by the block mover/reader 200 when performing DMA transfers The operating modes of the block mover/reader 200 are controlled by the block move control state machine 202 which is activated as described below. The clock and reset control signals are provided by the block move control state machine 202 to the other blocks depicted in FIG. 5 when its operation is activated. The clock signals (not shown in FIG. 5 are applied to most blocks to trigger their operations. The reset control signal (not shown in FIG. 5), derived from the POR signal, is applied to the state machine 202 and the counters and registers depicted in FIG. 5 to set them to a predetermined state when battery power is first applied.

Figure 6:
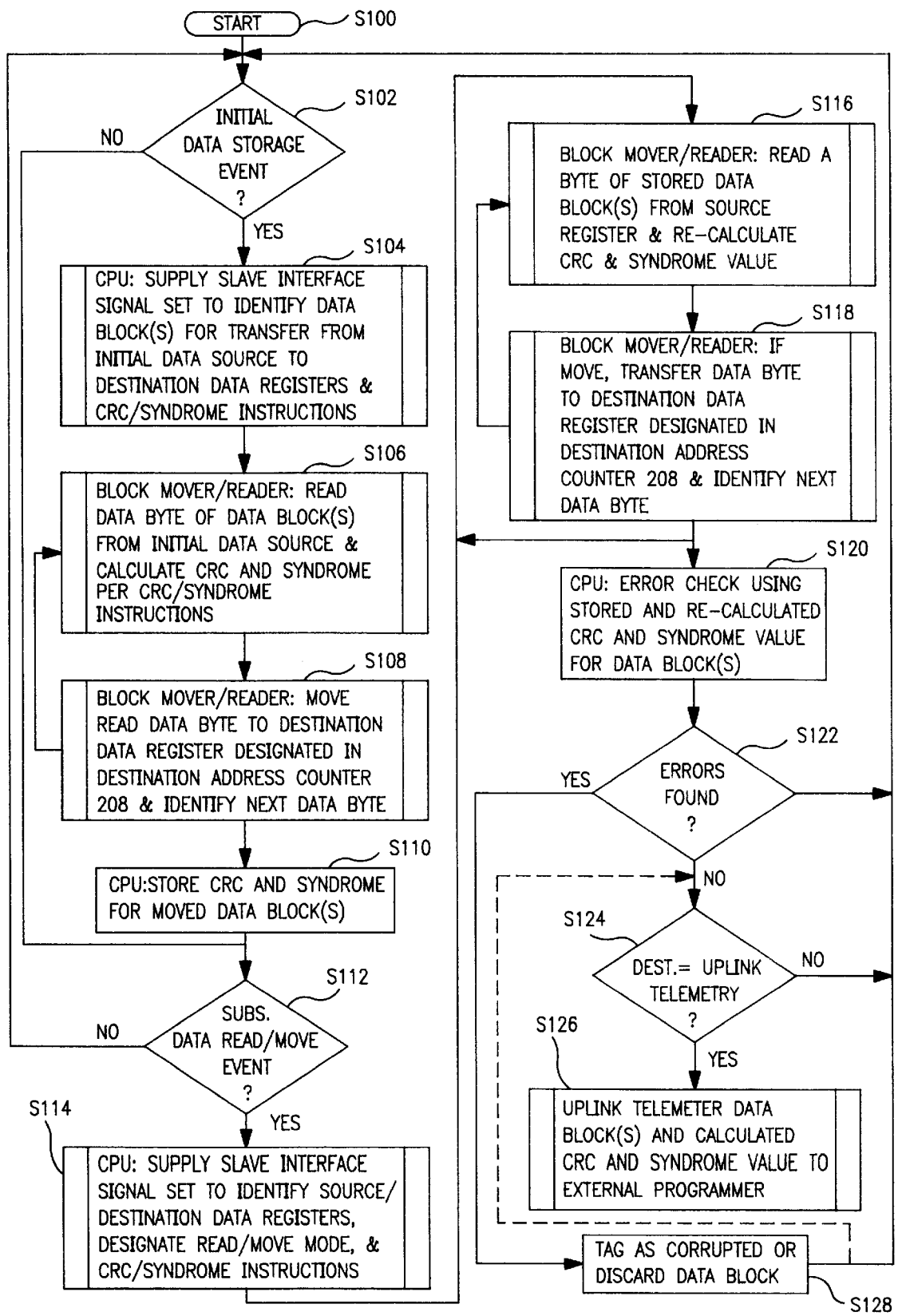
FIG. 6 illustrates the general method of calculation and use of a data CRC and optionally a syndrome value for a data block or series of data blocks in a block read/move operation in accordance with the present invention.
Figures 7, 8:
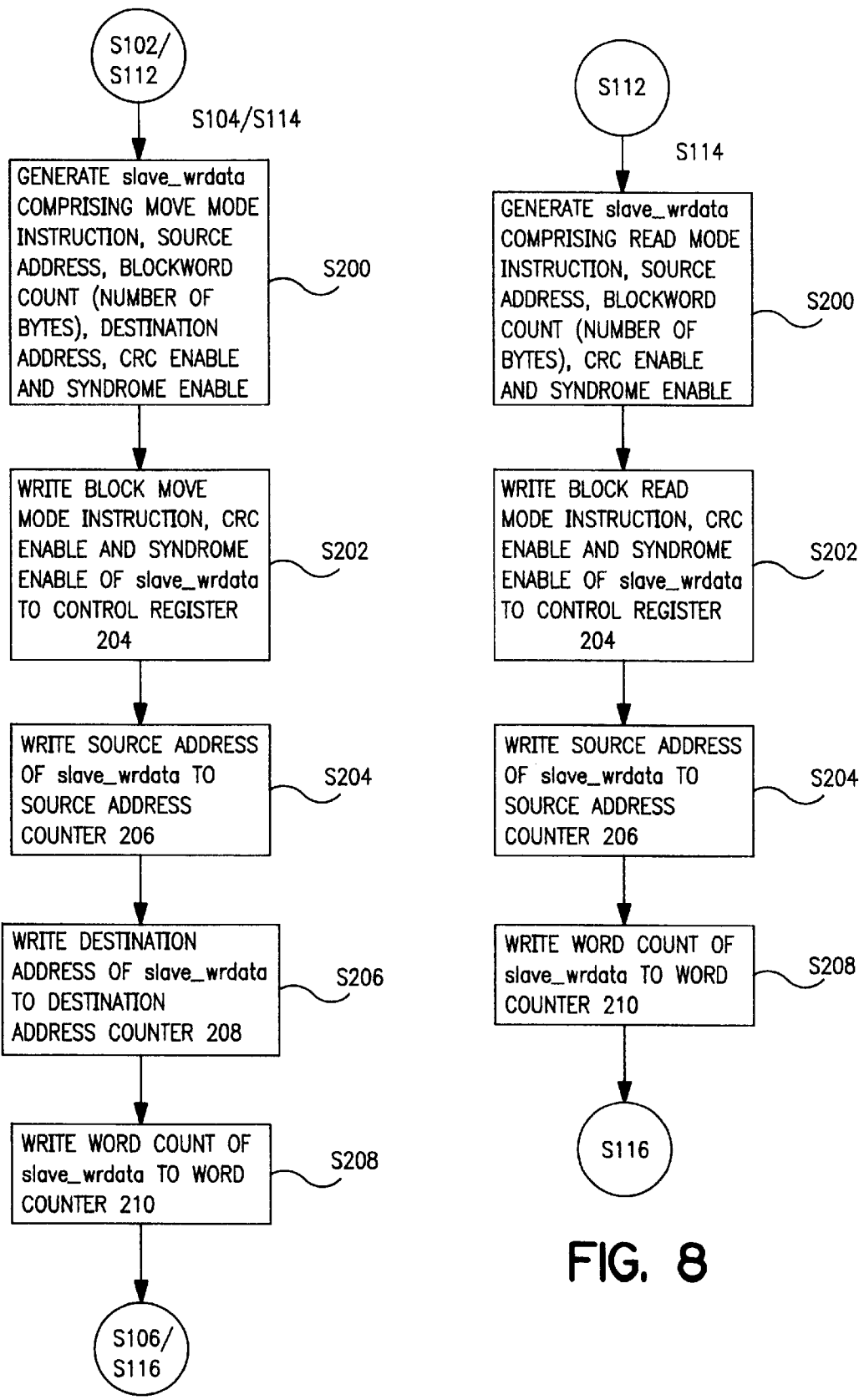
FIG. 7 illustrates in expanded detail steps set forth in FIG. 6 for generating a slave interface data set by the microcomputer of the ICD of FIGS. 2 and 3 and writing that data set to registers and counters of the block mover/reader of FIG. 5 to initiate a data block move.
FIG. 8 illustrates in expanded detail steps set forth in FIG. 6 for generating a slave interface data set by the microcomputer of the ICD of FIGS. 2 and 3 and writing that data set to registers and counters of the block mover/reader of FIG. 5 to initiate a data block read.
Figure 9:
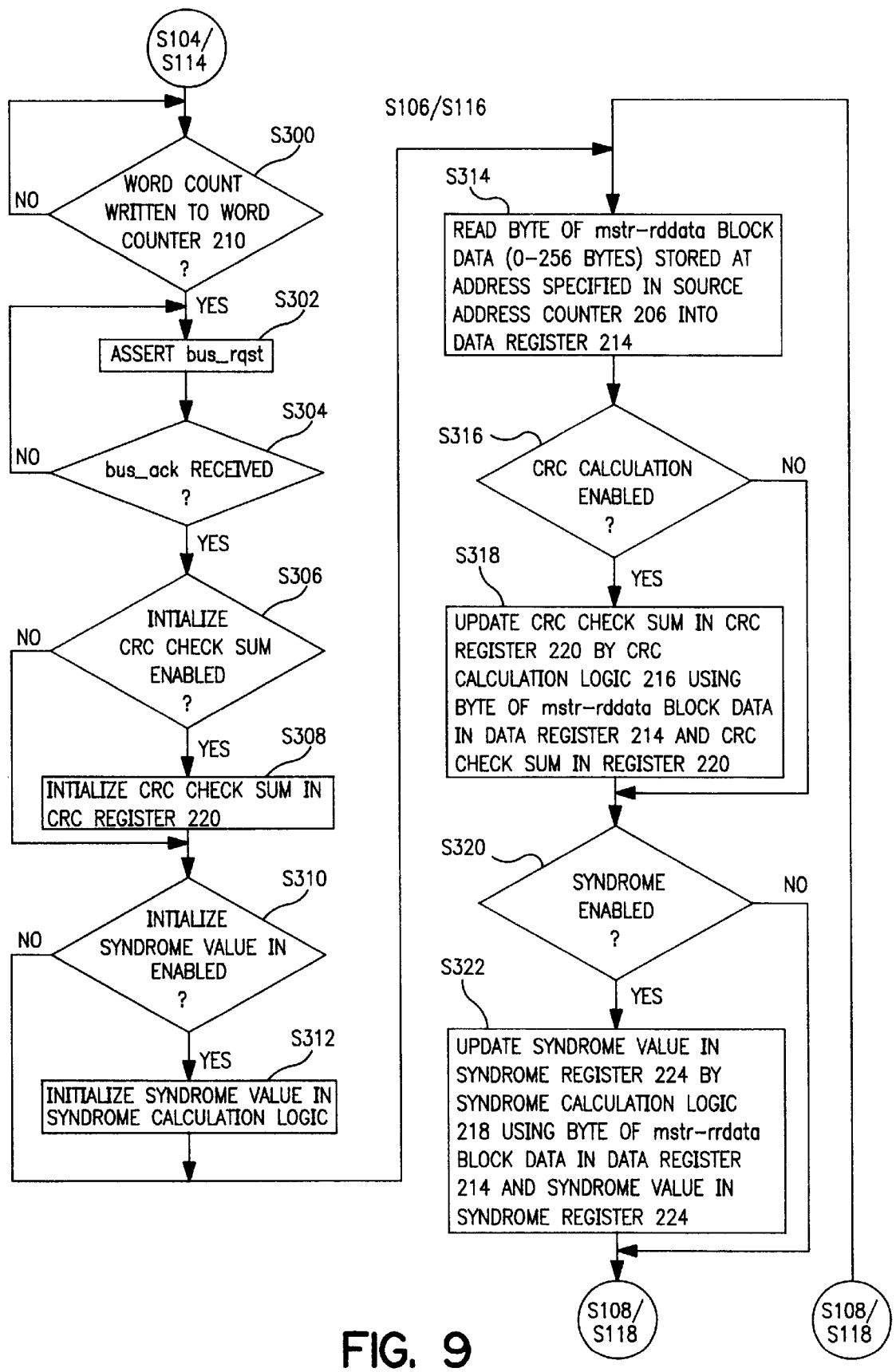
FIG. 9 illustrates in expanded detail steps set forth in FIG. 6 for calculating a CRC check sum and a syndrome value, when enabled, by the block mover/reader of FIG. 5.
Figure 10:
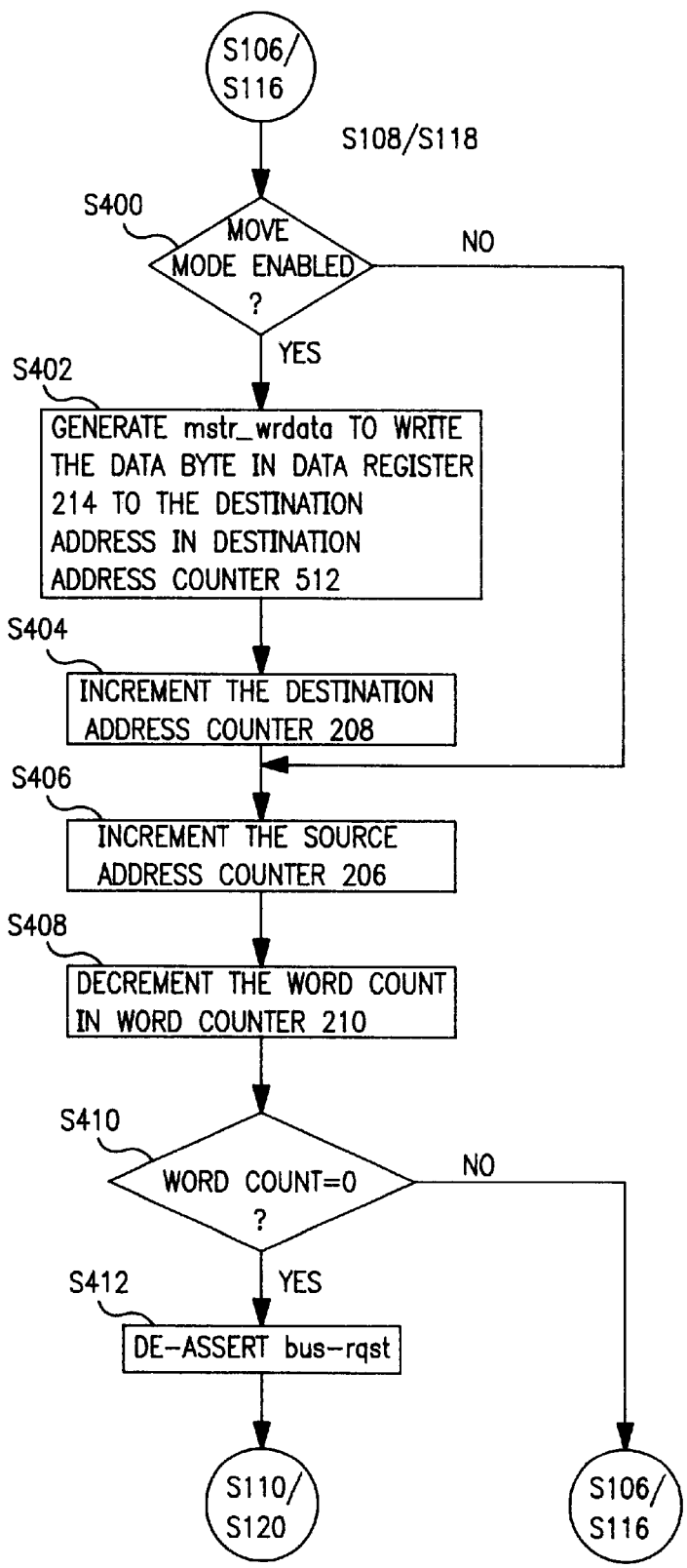
FIG. 10 illustrates in expanded detail steps set forth in FIG. 6 for identifying the next data byte in a data block for processing in accordance with FIG. 9 and for moving, if a data move mode is enabled, the processed data byte of the data block to a destination register.

The blocks and signals of FIG. 5 are best explained in relation to their functions during a block move or read operation initiated by the CPU 150. FIG. 6 illustrates the general method of calculation and use of a data CRC and optionally a syndrome value for a data block or series of data blocks in a block read/move operation comprising steps S100 through S128 that are performed by the CPU 150 or the block mover/reader 200 with the use of other components of the ICD operating system 100. FIGS. 7 and 8 illustrate step S104 or S114 of FIG. 6 in expanded detail as alternate steps S200–S208 for generating a slave interface data set by CPU 150 and writing that slave data set to registers and counters of the block mover/reader 200 to initiate a data block move or read operation. FIG. 9 illustrates steps S106 and S116 of FIG. 6 in expanded detail as steps S300–S322 for reading each data byte or word of the data block(s) and calculating a CRC check sum and a syndrome value, when enabled, by the block mover/reader 200. FIG. 10 illustrates steps S108 and S118 of FIG. 6 in expanded detail as steps S400–S412 for identifying the next data byte in a data block for processing, in accordance with steps S314–S322 of FIG. 9, and for moving, if a data move mode is enabled, the processed data byte of the data block to a destination register.

It takes two clock cycles per byte for the block mover/reader 200 to transfer an 8-bit data word from a source memory register to a destination memory register. In the first clock cycle, the state machine 202 enables a mstr_rddata byte read from a source memory location or register accessed using the source register address in the source address counter 206 into the data register 214. During that clock cycle, the state machine 202 selectively enables the calculation of the CRC and syndrome value loaded into CRC register 220 and syndrome register 224, respectively. The mstr_wrdata is written to the destination memory location or register during the second clock cycle. Assuming a 1.4 MHz oscillator, each clock duration is 1.43 $\mu$sec, so that the transfer time is 2.86 $\mu$sec per byte. When operating in read only mode, there is only one clock per transfer, since there is no write cycle. Therefore, the transfer time from the source register to the data register and calculation of the CRC and syndrome takes 1.43 $\mu$sec per byte. Thus, the maximum duration of a read and move of a 256 byte data block is less than 750 $\mu$sec.

In FIG. 6, at step S100 the method of the present invention is enabled in a standby mode. At some arbitrary or fixed time, either an initial data storage event occurs at step S102, wherein IMD data of any of the types described above is initially generated due to an operation of the CPU 150 and/or the pace/sense timing and control circuit 170, or a subsequent data read or move event is triggered at step S112. For example, in the former case, the scheduled daily measurement of lead impedance values or the detection of an arrhythmia triggering EGM data storage can constitute an initial data storage event wherein a block of data bytes are initially generated and read and can be temporarily stored in a temporary register or buffer. In the latter case, data that has already been stored in a register in SRAM 158 following the steps S104–S110 is identified to be read or moved to another destination register or to be read and telemetered out in an uplink telemetry transmission. A CRC and optionally a syndrome error checking routine is conducted in accordance with the present invention in steps S122 and S124.

Commencing with the initial storage of IMD data, at step S104, the CPU 150 generates a slave interface signal set that formulates the data into a data block or blocks, identifies where it is to be stored or written to and provides the enabling commands for CRC and/or syndrome value calculation. The block mover/reader 200 responds to the slave interface signal set in step S106, and calculates the CRC and syndrome address value, when enabled, from a data byte or word of the data block each time that the data byte is retrieved and read. In step S108, the block mover/reader 200 writes the data byte processed in step S106 to the destination register addressed using the DMA 160 and retrieves the next data byte for processing in step S106. The CRC and syndrome value are stored in a memory register in step S110 after all data bytes of the block or a series of blocks are processed in steps S106 and S108.

Step S104 (and step S114 in the data move mode, described below), is directed to the block move function and is depicted in greater detail in FIG. 7. In step S200, the slave interface data set described above is generated by CPU 150 and comprises the slave write data (slave_wrdata), the slave address (slav_addr) instruction; the chip select (cs) instruction, the slave read (slav_rd) enable instruction and the slave write (slav_wr) enable instruction. In step S200, the cs, slav_rd and slav_wr instructions and slav_adrs data are also applied to the address decode logic 212. The address decode logic 212 uses them to route parts of the slav_wrdata to the respective ones of the control register 204, source address counter 206, destination address counter 208 and word counter 210.

Thus, in step S202, selective bits of the slave_wrdata word are routed to the control register 204 which is read by the state machine 202 to conduct a block read or move and to enable CRC or syndrome value calculation and to selectively enable operation and initialization of each of the CRC and/or syndrome registers 220 and 224, respectively. In steps S206 and S208, other parts of the slave_wrdata are directed to the source address counter 206 and the destination address counter 208, respectively, to set their hexadecimal counts to the first byte source address of the data block to be read and moved and the first byte destination address that the data block is to be moved to, respectively. In step S208, the word counter 210 is loaded with a word count within the slav_wrdata representing the number of data bytes (1–256) of the data block. In this way, the CPU 150 loads these counters and registers of the block mover/reader 200 to commence the block read and move operation. Each data block is identified by length (number of bytes or words) and address for transfer from an initial storage buffer in RAM 152 or separate dedicated buffers to permanent memory registers in SRAM 158. The calculated CRC and syndrome values are routed to destination registers that can be associated with the data block or maintained in dedicated registers in RAM 152 or SRAM 158.

At this point, it is desirable to conduct the block read and move operation while the CPU 150 is dormant and interrupts are disabled. Returning to FIG. 5 and in reference to FIG. 6, in step S106, the block mover/reader 200 takes over and conducts a master read data (mstr_rddata) retrieval to load a data byte identified in the source address counter 206 into the parallel data register 214. The CRC and syndrome calculations (if enabled) are made in step S106, and the data byte in data register 214 is then written as master write data (mstr_wrdata) to the destination address loaded in destination address counter 208 in step S108. The next data byte of the data block is identified in step S108, and the process is repeated in step S106 upon the next data byte until all data bytes are retrieved, read, processed and moved through the block mover/reader 200. In step S110, the 16-bit CRC and syndrome value accumulated in the 16-bit CRC register 220 and syndrome register 224 are transferred to destination registers through destination data MUX 228 after all the mstr_wrdata words are transferred as described further below.

Step S106 (and step S116, as described below) is expanded in FIG. 9 to show how the CRC and syndrome value are calculated in the block mover/reader 200 of FIG. 5. The initial operations in response to the slave_wrdata loaded into control register 204 are set forth in steps S300–S312. Then, the read and error code calculation steps S314–S322 are followed for the initial data byte and each subsequent data byte of the data block(s) until all data bytes are read as determined in step S108 (and step S118 as described below).

In step S300, the block move control state machine 202 detects the setting of a word count in word counter 210 conducted in step S208 and generates the bus request (bus_rqst) signal that is asserted on data/control line 148 to the CPU 150. The DMA controller 160 responds by generating the bus acknowledgment (bus_ack) signal that is detected in step S304 and relinquishes control of the data/control bus 148 until the bus_rqst is no longer asserted or until the watchdog 180 times out.

The error code calculations for an IMD data block or series of blocks in accordance with the present invention can be selectively enabled or disabled by a programmed instruction. And, if enabled, then the register in which the error code is accumulated during the reading of the data bytes of the IMD data block(s) can be selectively initialized. Initialization is typically enabled if only a single block of up to 256 data bytes is to be subjected to a block read and move so that the CRC and/or syndrome is generated for that specific data block. However, more than one data block can be sequentially read and moved, and a single CRC and/or syndrome value can be calculated for the series of IMD data blocks.

In step S306, the state machine 202 determines if the initialization of the CRC register 220 to a known state, e.g. all "ones", is enabled by the slave_wr data in control register 204. If initialization is enabled, the CRC register 220 is initialized in step S308. Similarly, in step S310, the state machine 202 determines if initialization of the syndrome register 224 to a known state, e.g. all "zeros", is enabled by the slave_wr data in control register 204. If initialization is enabled, the syndrome register 224 is initialized in step S312. These preliminary steps S300–S312 are not repeated during the subsequent processing of the data bytes in accordance with steps S314–S322.

In step S314, the block move control state machine 202 causes the source address in source address counter 206 to be passed through the MUX 228 and read by the DMA 160 which retrieves the mstr_rddata word (the first data byte) and sends it to the data register 214.

The CRC calculation is conducted in step S318 by the CRC calculation logic 216 if the CRC calculation is enabled as determined in step S316. The CRC calculation logic 216 operates on the accumulated or initialized CRC in the CRC register 220, the mstr_rddata word in data register 214, and the CRC polynomial function during the first clock cycle as the mstr_rddata word is read into the data register 214. The 16-bit CRC is calculated by CRC calculation logic 216 using the CRC-CCITT polynomial, which is given by: $x^{16}+x^{12}+x^5+1$.

The syndrome calculation is conducted in step S322 by the syndrome calculation logic 218 if the syndrome calculation is enabled as determined in step S320. The syndrome calculation logic 218 operates on the accumulated or initialized syndrome value in the syndrome register 224, the mstr_rddata word in data register 214 and the syndrome polynomial function during the first clock cycle as the mstr_rddata word is read into the data register 214. The syndrome generation provides a method of 2 bit error detection and 1 bit error correction of EEPROM data or other RAM data The modified Hamming Code can be used on blocks up to 256 bytes long. The syndrome generator block is a linear feedback shift register (LFSR) that generates a unique signature when data is shifted through it. The characteristic polynomial algorithm used in the syndrome calculation is: $P(x)=1+x^4+x^5+x^8+x^9+x^{11}+x^{12}+x^{16}$.

Steps S314–S322 are repeated for each data byte of the IMD data block(s) identified in step S104 to accumulate a CRC and syndrome value, if enabled, in CRC register 220 and syndrome register 224 during the first clock cycle as each IMD data byte is read into the register 214.

In the second clock cycle, step S108 of FIG. 6 is completed which, in this case, includes the data move operation as determined in step S400 of FIG. 10 by the state machine 202 from the contents of the control register 204. In step S402, the state machine 202 supplies a write instruction on data/control bus 148 to move the mstr_wrdata in data register 214 to the destination address in the destination address counter 208 which is read as mstr_adrs data through the MUX 228. In steps S404 and S406 the source and destination address counters 206 and 208, respectively, are incremented, and the word count in word counter 210 is decremented in step S408.

The word count is read by the state machine 202, and compared to zero in step S410. If the word count is not decremented to zero, the steps S106 and S108 are repeated for the next data byte of the data block. In this way, each IMD data block is directed on data/control bus 148 through the block reader/mover 200 a data byte at a time and the enabled CRC and syndrome values are calculated for the data block (or a series of data blocks). Each data byte of the data block(s) is routed back onto the data/control bus 148 for storage in the designated destination registers in SRAM 158.

If the word count is decremented to zero as determined in step S410, then all data bytes of the data block(s) have been read and moved, and the state machine de-asserts the bus_rqst signal in step S412 and moves to step S110 of FIG. 6. In step S110, the address decoder 212 and MUX 226 are employed by the CPU 150 to read the contents of the CRC register 220, the syndrome register 224, the control register 204 and the source and destination address counts in counters 206 and 208, respectively. The values in the CRC register 220 and the syndrome register 224 are then stored in memory via MUX 226 by the CPU 150.

At a subsequent time, a data/read move event is initiated by CPU 150 in step S112 of FIG. 6, wherein the CRC and syndrome value for the same data block(s) are recalculated in the block mover/reader 200 and compared to the previously calculated CRC and syndrome value stored in step S110 for determination if they are the same or have changed. The subsequent data read/move event may be a scheduled block read operation for error checking the data block or it may constitute a data move operation to new destination registers in SRAM 158. The data block read or move operation can also be conducted in conjunction with uplink telemetry of data blocks in steps S124 and S126 initiated by receipt of an interrogation command by telemetry I/O registers and control block 164.

In step S114, the slave interface signal set is generated by the CPU, and steps S200, S202, S204, and S208 of FIG. 8 are followed as described above. In this case, it is presumed that a read only mode is enabled to provide the re-calculated CRC and syndrome value, but it will be understood that a read and move mode can be enabled, in which case step S206 of FIG. 7 would be invoked. Step S116 retraces steps S300 to S322 of FIG. 9 to generate the re-calculated CRC and syndrome value for the data block(s).

In steps S120 and S122, error determination is made by CPU 150 preferably using the re-calculated CRC read from the CRC register 220 and optionally the re-calculated syndrome value read from the syndrome register 224 via MUX 226. With respect to the CRC, in step S120, the stored CRC for the data block(s) is retrieved by the CPU 150 from other memory and compared to the CRC recalculated in step S116. The results of the comparison are determined in step S122, and the results of the comparison are used to discard or tag IMD data block corrupted since the time that the associated error code was calculated and stored in step S128. This CRC re-calculation and comparison can detect all errors spanning 16 contiguous bits (2 bytes) or less and detect 99.998% of the remaining errors. The fraction of errors detected is independent of the data block size, although as the block size increases, the absolute number of undetected errors increases.

Optionally, the syndrome value is also re-calculated in step S120 by syndrome calculation logic 218 and accumulated in the 16-bit syndrome register 224 as each byte of data of the data block(s) is re-read. The stored syndrome value (stored in memory in association with the block(s) of IMD data upon their initial storage in IMD memory) is retrieved by CPU 150. When all bytes of the block(s) of IMD data are re-read, the retrieved syndrome value is read into the syndrome register 224 and the resultant value is read by CPU 150 through MUX 226.

If the syndrome values are the same, the resultant value in 16-bit syndrome register 224 will be reduced to a known quantity, e.g., all "zeros". But, if an error has occurred in a data bit among the re-read data block(s), then the resultant syndrome value will be a binary number that points to the erroneous bit among the data bytes of the data block(s). If a single error bit exists in the reread block(s), the value left in the syndrome register 224 can be used by a firmware algorithm to identify the bit that was in error. A double bit error will be indicated, but the error cannot be located or corrected. If more than two bits are in error, they may not be indicated by the resultant number in the syndrome register 224.

If the subsequent data read/move event that satisfied decision step S112 is an interrogation and uplink telemetry transmission of the data blocks in steps S124 and S126, then the data blocks can be uplink telemetered with their CRC and syndrome values. The transmission would ordinarily only comprise valid data blocks and their associated data CRC and syndrome values, but it would be possible to transmit corrupted data blocks and their associated data CRC and syndrome values if that were to be considered useful. A further telemetry CRC may be calculated and appended to the uplink telemetered data blocks and data CRC and syndrome value in the manner described in the above-referenced '404 patent, for example.

The external programmer receiving the uplink telemetry transmissions can employ CRC and syndrome calculation software or hardware to check both the telemetry CRC and the data CRC and syndrome. In this way, a high assurance can be obtained that the uplink telemetered data is not contaminated or corrupted.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

What is claimed is:

1. An implantable medical device adapted to be implanted in a patient's body for providing a therapy to a patient and/or monitoring a condition of a patient and storing device data comprising:

implantable device memory comprising a plurality of memory registers having memory addresses in which blocks of device data can be selectively stored;

storing means for storing blocks of device data in memory registers at specified memory register addresses;

block read means for selecting and reading blocks of device data from specified memory register addresses;

error code calculating means for calculating an error code from a selected and read block of device data as the block of device data is read; and error code storage means for storing the error code calculated from the selected and read block of device data.

2. The implantable medical device of claim 1, wherein: said error code calculating means calculates an error code from a plurality of blocks of selectively read device data.

3. The implantable medical device of claim 2, wherein said error code comprises a cyclic redundancy code.

4. The implantable medical device of claim 2, wherein said error code comprises a syndrome value.

5. The implantable medical device of claim 2, further comprising:

telemetry means for transmitting the error code and the blocks of device data that it is calculated from to a telemetry transmission receiver external to the patient's body.

6. The implantable medical device of claim 2, wherein: said block read means further comprises means for addressing the plurality of memory registers to retrieve selected blocks of device data from source registers; and further comprising:

block move means for moving the selected blocks of data read by said block read means to destination registers of said device memory.

7. The implantable medical device of claim 2, further comprising:

means for selectively commencing the operation of said block read means and said error code calculating means and re-calculating a re-calculated error code from the blocks of device data; and means for comparing the stored error code to the re-calculated error code and determining if the re-calculated error code indicates that an error has occurred in the blocks of device data.

8. The implantable medical device of claim 1, wherein: said block read means further comprises means for addressing the plurality of memory registers to retrieve selected blocks of device data from source registers; and further comprising:

block move means for moving the selected blocks of data read by said block read means to destination registers of said device memory.

9. The implantable medical device of claim 1, further comprising:

telemetry means for transmitting the error code and the block of device data that the error code is calculated from to a telemetry transmission receiver external to the patient's body.

10. The implantable medical device of claim 1, wherein said error code comprises a cyclic redundancy code.

11. The implantable medical device of claim 1, wherein said error code comprises a syndrome value.

12. The implantable medical device of claim 1, further comprising:

means for selectively commencing the operation of said block read means and said error code calculating means and re-calculating a re-calculated error code from the block of device data; and means for comparing the stored error code to the re-calculated error code and determining if the re-calculated error code indicates that an error has occurred in the block of device data.

13. The implantable medical device of claim 1, further comprising:

memory means for storing implantable medical device operating mode and parameter value instructions;

means for operating the implantable medical device in accordance with the stored operating modes and parameter value instructions; and means for monitoring at least one operating condition of the implantable medical device and for deriving device operating data therefrom; and wherein:

said device data further comprises such device operating data and stored operating modes and parameter value instructions.

14. In an implantable medical device adapted to be implanted in a patient's body for providing a therapy to a patient and/or monitoring a condition of a patient to derive device data therefrom and for storing the device data, the method comprising:

storing device data in a plurality of memory registers at specified memory addresses;

selecting and reading at least one block of stored device data;

calculating an error code from a selected and read block of device data as the block of device data is read; and storing the error code calculated from the selected and read block of device data.

15. The method of claim 14, wherein: said error code calculating step comprises calculating an error code from a plurality of blocks of selectively read device data.

16. The method of claim 15, wherein said error code comprises a cyclic redundancy code.

17. The method of claim 15, wherein said error code comprises a syndrome value.

18. The method of claim 15, further comprising the step of:
transmitting the error code and the blocks of device data that it is calculated from to a telemetry transmission receiver external to the patient's body.

19. The method of claim 15, further comprising the steps of:
selecting and re-reading the blocks of stored device data;
re-calculating an error code from a selected and re-read blocks of device data as the block of device data is re-read and providing a re-calculated error code; and
comparing the stored error code to the re-calculated error code and determining if the recalculated error code indicates that an error has occurred in the blocks of device data.

20. The method of claim 15, wherein:
said reading step further comprises addressing the plurality of memory registers to retrieve selected blocks of device data from source registers thereof; and
further comprising the step of:
moving the selected blocks of data read in said reading step to destination registers of said device memory.

21. The method of claim 14, wherein said error code comprises a cyclic redundancy code.

22. The method of claim 14, wherein said error code comprises a syndrome value.

23. The method of claim 14, further comprising the step of:
transmitting the error code and the block of device data that it is calculated from to a telemetry transmission receiver external to the patient's body.

24. The method of claim 14, further comprising the steps of:
selecting and re-reading the block of stored device data;
re-calculating an error code from a selectively read block of device data as the block of device data is re-read and providing a re-calculated error code; and
comparing the stored error code to the re-calculated error code and determining if the re-calculated error code indicates that an error has occurred in the block of device data.

25. The method of claim 14, further comprising the steps of:
storing implantable medical device operating mode and parameter value instructions;
operating the implantable medical device in accordance with the stored operating modes and parameter value instructions; and
monitoring at least one operating condition of the implantable medical device and deriving device operating data therefrom; and wherein:
said device data further comprises such device operating data and stored operating modes and parameter value instructions.

26. A programmable implantable medical device adapted to be implanted in a patient's body for delivering a therapy to a patient and/or monitoring a condition of a patient, the implantable medical device operating in accordance with operating modes and parameters established by stored operating instructions and further operable to monitor at least one condition of the device, the implantable medical device further comprising:
means for compiling device data bytes from device data sources comprising one or more of the delivery of device therapies, monitored device conditions, monitored conditions of the patient, and stored operating instructions;
device memory comprising a plurality of memory registers in which blocks of device data each comprising a plurality of data bytes are selectively stored at memory addresses;
retrieval means for addressing the memory addresses of the plurality of memory registers to retrieve a block or blocks of device data a data byte at a time;
block read means for selectively reading each data byte of the block or blocks of device data retrieved from the source registers addressed by said retrieval means;
error code calculating means for calculating an error code from the data bytes of the selectively read block or blocks of device data as the data bytes of the block or blocks of device data are read by said block read means; and
error code storage means for storing the error code calculated from the selectively read block or blocks of device data.

27. The implantable medical device of claim 26, further comprising:
block move means for moving the data bytes read by said block read means to destination registers of said device memory.

28. The implantable medical device of claim 27, further comprising:
means for selectively commencing the operation of said retrieval means, said block read means and said error code calculating means and re-calculating a re-calculated error code from the block or blocks of device data; and
means for comparing the stored error code to the re-calculated error code and determining if the re-calculated error code indicates that an error has occurred in the block or blocks of device data.

29. The implantable medical device of claim 26, further comprising:
means for selectively commencing the operation of said retrieval means, said block read means and said error code calculating means and re-calculating a re-calculated error code from the block or blocks of device data; and
means for comparing the stored error code to the re-calculated error code and determining if the re-calculated error code indicates that an error has occurred in the block or blocks of device data.

30. A method of operation of a programmable implantable medical device adapted to be implanted in a patient's body for delivering a therapy to a patient and/or monitoring a condition of a patient, the implantable medical device operating in accordance with operating modes and parameters established by stored operating instructions and further operable to monitor at least one condition of the device, the method further comprising the steps of:
compiling device data bytes from device data sources comprising one or more of the delivery of device therapies, monitored device conditions, monitored conditions of the patient, and stored operating instructions;
storing block or blocks of device data each comprising a plurality of device data bytes in device memory registers having register addresses;
addressing the memory addresses of the plurality of memory registers to retrieve a block or blocks of device data a data byte at a time;

reading each data byte of a block or blocks of device data retrieved from the source registers;

calculating an error code from the data bytes as the data bytes of the block or blocks of device data are read; and storing the error code calculated from the read block or blocks of device data.

31. The method of claim 30, further comprising the step of:

moving the data bytes read during the reading step to destination registers of said device memory.

32. The method of claim 31, further comprising the steps of:

retrieving an error code of a previously read block or blocks of device data;

addressing the memory addresses of the plurality of memory registers to retrieve the previously read block or blocks of device data a data byte at a time;

re-reading each data byte of the retrieved block or blocks of previously read device data;

re-calculating a re-calculated error code from the data bytes as the data bytes of the block or blocks of device data are re-read;

comparing the stored error code to the recalculated error code; and determining if the re-calculated error code indicates that an error has occurred in the block or blocks of device data.

33. The method of claim 30, further comprising the steps of:

retrieving an error code of a previously read block or blocks of device data;

addressing the memory addresses of the plurality of memory registers to retrieve the previously read block or blocks of device data a data byte at a time;

re-reading each data byte of the retrieved block or blocks of previously read device data;

re-calculating a re-calculated error code from the data bytes as the data bytes of the block or blocks of device data are re-read;

comparing the stored error code to the re-calculated error code; and determining if the re-calculated error code indicates that an error has occurred in the block or blocks of device data.

* * * * *

UNITED STATES PATENT AND TRADEMARK OFFICE
CERTIFICATE OF CORRECTION

PATENT NO. : 6,128,528
DATED : October 3, 2000
INVENTOR(S) : Ericksen et al.

It is certified that error appears in the above-identified patent and that said Letters Patent is hereby corrected as shown below:

Title page,
Item [73], Assignee: "Medtronics, Inc." should read -- Medtronic, Inc. --

Signed and Sealed this

Twenty-fifth Day of December, 2001

Attest:

Attesting Officer

JAMES E. ROGAN
Director of the United States Patent and Trademark Office